US012378174B2

(12) United States Patent
Werner et al.

(10) Patent No.: US 12,378,174 B2
(45) Date of Patent: Aug. 5, 2025

(54) PROCESS FOR PRODUCING 1-(4-ISOBUTYLPHENYL)ETHANOL BY HYDROGENATION OF 1-(4-ISOBUTYL-PHENYL)ETHANONE IN THE PRESENCE OF A CATALYST COMPOSITION COMPRISING COPPER

(71) Applicant: BASF SE, Ludwigshafen (DE)

(72) Inventors: Albert Werner, Bishop, TX (US); Annebart Wentink, Bishop, TX (US); Simon Kokolakis, Ludwigshafen (DE); Andreas Weickgenannt, Ludwigshafen (DE); Rolf Pinkos, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 473 days.

(21) Appl. No.: 17/298,692

(22) PCT Filed: Dec. 2, 2019

(86) PCT No.: PCT/EP2019/083236
§ 371 (c)(1),
(2) Date: Jun. 1, 2021

(87) PCT Pub. No.: WO2020/114938
PCT Pub. Date: Jun. 11, 2020

(65) Prior Publication Data
US 2022/0041533 A1 Feb. 10, 2022

(30) Foreign Application Priority Data
Dec. 3, 2018 (EP) ..................... 18209844

(51) Int. Cl.
*C07C 29/145* (2006.01)
*B01J 8/04* (2006.01)
*B01J 19/14* (2006.01)
*B01J 19/24* (2006.01)
*B01J 21/04* (2006.01)
*B01J 21/08* (2006.01)
*B01J 23/72* (2006.01)
*B01J 23/78* (2006.01)
*B01J 23/80* (2006.01)
*B01J 23/889* (2006.01)

(52) U.S. Cl.
CPC ............ *C07C 29/145* (2013.01); *B01J 8/04* (2013.01); *B01J 19/14* (2013.01); *B01J 19/245* (2013.01); *B01J 19/2465* (2013.01); *B01J 21/04* (2013.01); *B01J 21/08* (2013.01); *B01J 23/72* (2013.01); *B01J 23/78* (2013.01); *B01J 23/80* (2013.01); *B01J 23/8892* (2013.01)

(58) Field of Classification Search
CPC combination set(s) only.
See application file for complete search history.

(56) References Cited

U.S. PATENT DOCUMENTS

| 4,990,681 A | 2/1991 | Curtis et al. | |
| 5,243,095 A * | 9/1993 | Roberts | B01J 23/8892 568/864 |
| 6,049,008 A * | 4/2000 | Roberts | B01J 37/0009 564/422 |
| 6,201,160 B1 * | 3/2001 | Brudermuller | C07C 29/175 502/305 |
| 6,410,806 B2 | 6/2002 | Oku et al. | |

FOREIGN PATENT DOCUMENTS

| CN | 1911883 A | 2/2007 | |
| CN | 102211041 A | 10/2011 | |
| CN | 107999082 A | 5/2018 | |
| EP | 0284310 A1 * | 9/1988 | ............ C07C 57/30 |
| EP | 0358420 A2 | 3/1990 | |
| JP | H05-078273 A | 3/1993 | |
| JP | 2001199917 A | 7/2001 | |
| JP | 2007045735 A | 2/2007 | |
| WO | WO-2018054755 A1 | 3/2018 | |

OTHER PUBLICATIONS

International Application No. PCT/EP2019/083236, International Preliminary Report on Patentability, dated Jun. 8, 2021.
International Application No. PCT/EP2019/083236, International Search Report and Written Opinion, mailed Feb. 4, 2020.
Lu et al., Chemical Abstracts Service (Apr. 22, 2016)—Synthesis of ibuprofen by hydrogenation-carbonylation of 4-isobutyl acetophenone, Qingdao Keji Daxue Xuebao, Ziran Kexueban, vol. 36 pp. 255-259 (2015).
Zaccheria et al., Heterogeneous selective catalytic hydrogenation of aryl ketones to alcohols without additives, Tetrahedron Lett., 46(21):3695-7 (2005).
Chen et al., Study on hydrogenation of pisobutylacetophenone over Pd/C catalyst, Journal of Catalysis, vol. 4, pp. 471-474 (1999).
Jian et al., Characterization of MgO/AC catalysts and their use in the characterization and its performance in the hydrogen transfer reaction of p-isobutylacetophenone, Petrochemical Products,41(6) 688-693 (2012).

* cited by examiner

*Primary Examiner* — Sikarl A Witherspoon
(74) *Attorney, Agent, or Firm* — Faegre Drinker Biddle & Reath LLP

(57) ABSTRACT

Described is a process for producing 1-(4-isobutylphenyl) ethanol by reacting 1-(4-isobutyl-phenyl)ethanone with hydrogen in the presence of a catalyst composition comprising cop-per and one or more metals other than copper, and a use of a respective composition and/or of a pre-composition, the pre-composition comprising a mixture of oxides of copper and oxides of one or more metals other than copper, in a catalytic hydrogenation process for producing 1-(4-isobutylphenyl)ethanol from 1-(4-isobutylphenyl)ethanone.

15 Claims, No Drawings

PROCESS FOR PRODUCING 1-(4-ISOBUTYLPHENYL)ETHANOL BY HYDROGENATION OF 1-(4-ISOBUTYL-PHENYL)ETHANONE IN THE PRESENCE OF A CATALYST COMPOSITION COMPRISING COPPER

CROSS-REFERENCE TO RELATED APPLICATIONS

This is the U.S. national phase of International Application No. PCT/EP2019/083236, filed Dec. 2, 2019, which claims the benefit of European Patent Application No. 18209844.2, filed on Dec. 3, 2018.

The present invention relates to a process for producing 1-(4-isobutylphenyl)ethanol by reacting 1-(4-isobutylphenyl)ethanone with hydrogen in the presence of a catalyst composition comprising copper and one or more metals other than copper, and to a use of a respective composition and/or of a pre-composition, the pre-composition comprising a mixture of oxides of copper and oxides of one or more metals other than copper, in a catalytic hydrogenation process for producing 1-(4-isobutylphenyl)ethanol from 1-(4-isobutylphenyl)ethanone.

1-(4-isobutylphenyl)ethanol (CAS RN 40150-92-3) is a key intermediate compound in processes for producing ibuprofen (INN; "IBU"), a nonsteroidal anti-inflammatory drug ("NSAID") compound known for its pain-relieving properties. Several processes are already available to produce phenyl-substituted alcohols, including 1-(4-isobutylphenyl)ethanol, by selective reduction of acetophenone derivatives, in particular of 1-(4-isobutylphenyl)ethanone (CAS RN 38861-78-8), applying catalytic methods:

Document EP 0 358 420 A2 discloses a process for the production of 1-(4-isobutylphenyl)ethanol (also referred to as "IBPE") comprising hydrogenating 4-isobutylacetophenone (also referred to as "IBAP") in the absence of a solvent, using as a catalyst a treated activated nickel catalyst, e.g. Raney® nickel.

F. Zaccheria et al., Tetrahedron Letters 46 (2005), 3695-3697, have reported of heterogeneous selective catalytic hydrogenation of aryl ketones to alcohols without additives, e.g. of 1-(4-isobutylphenyl)ethanone. Reported experiments pertain to using a supported copper catalyst in the presence of a solvent in batch mode.

Document WO 2007/006719 A1 describes a catalyst and a method for hydrogenating carbonyl compounds.

In the light of the known prior art, there is still a need for a process to produce 1-(4-isobutylphenyl)ethanol with increased efficiency, e.g. in terms of selectivity of the reaction, which process can be carried out as a continuous process, i.e. suitable for larger-scale industrial production. For example, there is still a need for a process to produce 1-(4-isobutylphenyl)ethanol wherein side-products, in particular 1-ethyl-4-isobutylbenzene, which is often a major side-product in known syntheses of 1-(4-isobutylphenyl)ethanol, are only formed to the smallest extent possible. Since 1-(4-isobutylphenyl)ethanol is commonly produced as an intermediate compound for the synthesis of ibuprofen, a process to produce 1-(4-isobutylphenyl)ethanol wherein the proportion of side-products is reduced when compared to processes known from the prior art has the advantage of simplifying the purification of 1-(4-isobutylphenyl)ethanol to comply with the high standards required for pharmaceutical products.

For economic and environmental reasons, there is also still a need for such a process that would only require the presence of the least possible number of chemicals and can e.g. be performed without the presence of solvents or additives other than the actual reactants, e.g. the starting compound (i.e. 1-(4-isobutylphenyl)ethanone). Ideally, such a process should also result in an increased yield of the compound 1-(4-isobutylphenyl)ethanol when compared to similar hydrogenation processes known from the prior art.

Correspondingly, it was a primary object of the present invention to provide a process to produce 1-(4-isobutylphenyl)ethanol with increased efficiency, in particular with increased selectivity, more in particular with a reduced proportion of or 1-ethyl-4-isobutylbenzene being formed as a side product, which can be carried out as a continuous process. It was also an object of the present invention to provide such improved process where the process requires the presence of a least possible number of chemicals and can e.g. be performed with the least possible amount of solvents or additives other than the starting compound and ideally without the presence of solvents. Another object of the present invention was to provide process alternatives resulting in an increased yield of 1-(4-isobutylphenyl)ethanol compared to processes known from the prior art.

It was a further object of the invention to provide new and useful uses of certain copper-containing catalyst compositions and to widen their field of application.

It has now been found that the primary object and other objects of the present invention can be accomplished by a process for producing 1-(4-isobutylphenyl)ethanol comprising the step:

S3) reacting 1-(4-isobutylphenyl)ethanone with hydrogen in the presence of a catalyst composition comprising copper and one or more metals other than copper,
wherein the catalyst composition comprises the copper in a total amount in the range of from 30 mass-% to 98 mass-%, relative to the total mass of metals present in the catalyst composition,
so that 1-(4-isobutylphenyl)ethanol results as a product.

The invention as well as preferred variants or alternatives and preferred combinations of parameters, properties and elements thereof are defined in the appended claims. Preferred aspects, details, modifications and advantages of the present invention are also defined and explained in the following description and in the examples stated below.

It has now been found that the process according to the present invention is highly efficient, requires only very low (if at all) amounts of solvents and ideally does not require the presence of additional solvents (other than the actual reactants and/or products or intermediate products created in the process of the invention) and is excellently suited for continuous operation, in particular in a fixed-bed reactor, for larger-scale industrial production. The process further provides a highly selective reduction of 1-(4-isobutylphenyl)ethanone at the ketone functional group vs. an undesired reduction of e.g. the aromatic ring ("high selectivity") and a high conversion of 1-(4-isobutylphenyl)ethanone, i.e. a high proportion of the starting compound 1-(4-isobutylphenyl)ethanone is converted into 1-(4-isobutylphenyl)ethanol (for a definition of the terms "selectivity" and "conversion" as used in the present text, see below).

It has also been found that preferred variants or alternatives of the process of the invention even allow increased yields of 1-(4-isobutylphenyl)ethanol compared with similar processes known from the prior art. In addition, in the process according to the invention only a very small amount of side-products, e.g. by isomerization of 1-(4-isobutylphenyl)ethanone or 1-(4-isobutylphenyl)ethanol or by formation of 1-ethyl-4-isobutylbenzene, are formed and the number and amount of side-products formed in the process according to the invention is at least comparable and in some cases is even lower than in similar processes known from the prior art. In particular, it has been found that the process according to the present invention allows to produce 1-(4-isobutylphenyl)ethanol with a very low formation of 1-ethyl-4-isobutylbenzene as a side product, preferably with a formation of 5 mole-%, more preferably of 3 mole-% and yet more preferably of 1 mole-% 1-ethyl-4-isobutylbenzene, relative to the molar amount of 1-(4-isobutylphenyl)ethanone used as a starting compound for producing 1-(4-isobutylphenyl)ethanol. A further benefit of the process according to the present invention found in own experiments is its long-term stability. It has been found that the beneficial catalyst performance of the process (in particular in terms of selectivity and conversion) is highly stable over extended periods of e.g. >8000 operating hours.

In the process according to the invention as defined above (step S3)), 1-(4-isobutylphenyl)ethanol of formula I:

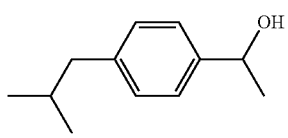

(I)

is formed as a (i.e the main) reaction product from 1-(4-isobutylphenyl)ethanone of formula II:

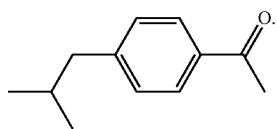

(II)

In the process according to the invention, the catalyst composition in step S3) comprises copper. The copper comprised by the catalyst composition is usually obtained by "activating" (i.e. reducing) a pre-catalyst composition—comprising a mixture of oxides of copper, preferably comprising copper-II-oxide (CuO), and oxides of one or more metals other than copper—with a reducing agent, usually hydrogen gas or a mixture of gases comprising hydrogen gas, or sometimes other known reducing agents, as is known in the art and as is further explained (and defined) below. The copper that is present in the catalyst composition in step S3) of the process of the invention is therefore usually present in the form as obtained after said "activating" of a respective or corresponding pre-catalyst composition.

In the process according to the present invention, the catalyst composition in step S3) also comprises one or more metals other than copper. Said one or more metals other than copper are also usually present in a form as obtained after "activating" (i.e. reducing) a respective (or corresponding) pre-catalyst composition—comprising a mixture of oxides of copper and oxides of one or more metals other than copper—with a reducing agent, as explained above and below. Said one or more metals other than copper can e.g. be present in the catalyst composition in the form of oxides of said one or more metals other than copper, or in other form. The one or more metals other than copper can be used alone or they can be used in combination. A combination of two or more metals other than copper is preferred in a catalyst composition for the purposes of the present invention.

The total amount of copper in the catalyst composition, relative to the total mass of metals present in the catalyst composition, is calculated for the purposes of the present invention as the ratio of the mass of copper atoms present in the catalyst composition, divided by the total mass of metal atoms present in the catalyst composition (see the examples section for a calculation example).

The total amount of copper and/or of one or more metals other than copper present in the catalyst composition in step S3) of the process according to the invention can be quantitatively determined by methods known in the art. In the context of the present invention, the total amount of copper and/or of one or more metals other than copper present in the catalyst composition in step S3) of the process according to the invention is preferably determined by X-ray Fluorescence Spectroscopy after (sample) fusion ("Röntgenfluoreszenzspektroskopie nach Schmelzaufschluss"), as is known in the art. Other suitable analytical methods for this same purpose which usually deliver the same or essentially the same results are Inductively Coupled Plasma Optical Emission Spectroscopy (ICP OES) after total digestion (of the sample) ("ICP OES nach Totalaufschluss") and Atomic Absorption Spectroscopy (AAS) measurement. Where necessary, the catalyst composition can be isolated from the reaction mixture by known methods and samples thereof can be prepared that are suitable for use in the relevant analytical method (preferably X-ray fluorescence spectroscopy after (sample) fusion) according to common methods known in the art.

In the process according to the invention, the catalyst composition in step S3) comprises copper and one or more metals other than copper. For the purposes of the present invention, a "metal" is a chemical element that stands in the periodic table of elements to the left and below (thus excluding hydrogen) of a line drawn from the element boron to the element astatine, where elements falling on this line (e.g. silicon and arsenic) are not counted as metals. As is common in the art, the term "metal" as used in the present text comprises transition metals, e.g. Cu, and main group metals, e.g. Ca, (where the term "main group" refers to the main groups of the periodic system of elements). Correspondingly, the term "metal atoms" as used in the present text comprises atoms of the metals according to the definition of "metal" above, i.e. atoms of transition metals (e.g. Cu) and atoms of main group metals (e.g. Ca, Na or Al).

Correspondingly, the term "metal oxide" as used in the present text comprises transition metal oxides (e.g. $MnO_2$) and main group metal oxides (e.g. $Na_2O$). The term "metal oxide" thus also comprises oxides of copper, in particular CuO and $Cu_2O$. Examples of "oxides of (one or more) metals other than copper" in the sense of the present invention are $Na_2O$, MgO, $Al_2O_3$, CaO, $Cr_2O_3$, $MnO_2$, ZnO, BaO, and $La_2O_3$.

In the context of the present invention and consistent with the usual meaning in the field, "conversion" means the percentage of chemical conversion of the starting compound 1-(4-isobutylphenyl)ethanone into one or more subsequent compounds in the course of the process according to the invention. For the purpose of the present invention, values of "conversion" are calculated by using formula III below:

$$100\% * (1 - [(\text{molar amount of 1-(4-isobutylphenyl)}\\\text{ethanone present at the end of step } S3))/(\text{molar}\\\text{amount of 1-(4-isobutylphenyl)ethanone present}\\\text{at the start of step } S3))]) \qquad \text{(III)}.$$

For the purpose of the present invention, the (relative) molar amounts of 1-(4-isobutylphenyl)ethanone present at the start and at the end of step S3) (in particular as used for calculations according to formula III) are in each case preferably determined by gas chromatography, as is known in the art.

In the context of the present invention and consistent with the usual meaning in the field, "selectivity" (in particular of the catalytic hydrogenation reaction of the process of the present invention) means the percentage of 1-(4-isobutylphenyl)ethanol which has been formed from the starting compound of 1-(4-isobutylphenyl)ethanone in the course of the process according to the invention. For the purpose of the present invention, values of "selectivity" are calculated by using formula IV below:

$$100\% * (\text{molar amount of 1-(4-isobutylphenyl)ethanol present at the end of step } S3)/(\text{converted molar amount of 1-(4-isobutylphenyl)ethanone}) \qquad (IV).$$

For the purpose of the present invention, the (relative) molar amount of 1-(4-isobutylphenyl)ethanol at the end of step S3) (in particular as used for calculations according to formula IV) is preferably determined by gas chromatography as is known in the art. The "conversion" used in the above-stated formula is the conversion as defined further above, see formula III.

A process according to the invention as defined herein (or a process according to the invention as described above or below as being preferred) is preferred, wherein the catalyst composition comprises the copper in a total amount in the range of from 45 mass-% to 98 mass-%, preferably of from 60 mass-% to 95 mass-% and more preferably of from 65 mass-% to 92.5 mass-%, relative to the total mass of metals present in the catalyst composition.

Preferred variants or alternatives (e.g. preferred metals other than copper and/or preferred proportions or preferred total amounts of copper in the catalyst composition) of the process according to the present invention as specified here above or below can preferably be combined and in case of their combination result in particularly preferred variants or alternatives of the process according to the invention.

It has been found in own experiments that a high proportion of copper, relative to the one or more metals other than copper in the catalyst composition present in step S3) of the process of the invention (and correspondingly a high proportion of copper oxides in the pre-catalyst composition present in step S1) and/or in step S2), see below) in the total amounts as defined above or below, is associated with increased efficiency of the hydrogenation process, in particular in terms of high product selectivity and high product yield.

Preferred is also a process according to the invention as defined herein (or a process according to the invention as described above or below as being preferred), wherein the catalyst composition comprises in addition to the copper:
c2) a carrier component comprising one or more substances selected from the group consisting of aluminium, aluminium compounds, silicon, silicon compounds, zirconium, zirconium compounds, carbon and carbon compounds,
wherein preferably the total amount of aluminium, silicon, zirconium and carbon in the catalyst composition, relative to the total mass of copper present in the catalyst composition, is in the range of from 2.5 mass-% to 60.0 mass-%, more preferably of from 3.0 mass-% to 35.0 mass-% and even more preferably of from 3.5 mass-% to 15.0 mass-%;
and/or (preferably "and")
c3) one or more metals not selected from the group consisting of copper, aluminium and zirconium,
wherein preferably the total amount of the one or more metals not selected from the group consisting of copper, aluminium and zirconium in the catalyst composition, relative to the total mass of metals present in the catalyst composition, is in the range of from 0.1 mass-% to 55.0 mass-%, more preferably of from 2.5 mass-% to 35.0 mass-% and even more preferably of from 5.0 mass-% to 30.0 mass-%.

The substances comprised by the carrier component (i.e. component c2) of the catalyst composition) can be used alone or they can be used in combination. For the purposes of the present invention it is preferred to only use substances of one single element in the carrier component (e.g. silicon and silicon compounds or aluminium and aluminium compounds).

For the avoidance of doubt, substances comprised by the carrier component that are or that comprise metals or metal compounds (i.e. aluminium, aluminium compounds, zirconium and zirconium compounds) are comprised by the definition of the "one or more metals other than copper" of the present invention (see above).

Substances comprised by the carrier component that are not metals or that do not comprise metals (e.g. silicon, silicon compounds, carbon and carbon compounds) are also usually present in the catalyst composition in a form as obtained after "activating" (i.e. reducing) a respective or corresponding pre-catalyst composition—comprising a mixture of oxides of copper and oxides of one or more metals other than copper—with a reducing agent, as explained above and below. Said substances that are not metals or that do not comprise metals can e.g. be present in the catalyst composition in the form of oxides (e.g. as $SiO_2$) or in other form, preferably in the form of oxides for aluminium, silicon and zirconium, and/or their respective compounds. The carbon that is present as a substance of the carrier component of the catalyst composition is preferably present as graphite.

The total amount of aluminium, silicon, zirconium and carbon in the catalyst composition, relative to the total mass of copper present in the catalyst composition, is calculated for the purposes of the present invention as the ratio of the total mass of aluminium atoms, silicon atoms, zirconium atoms and carbon atoms present in the catalyst composition (i.e. present as part of the aluminium, aluminium compounds, silicon, silicon compounds, zirconium, zirconium compounds, carbon and carbon compounds of component c2)), divided by the total mass of copper atoms present in the catalyst composition (see the examples section for a calculation example). For the avoidance of doubt, aluminium and zirconium are to be taken into account for calculating the total mass of metals present in the catalyst composition.

The one or more metals not selected from the group consisting of copper, aluminium and zirconium in the catalyst composition (i.e. component c2) of the catalyst composition of the above-defined preferred variant of the process according to the present invention) are comprised by the definition of the "one or more metals other than copper" of the present invention (see above).

The total amount of one or more metals not selected from the group consisting of copper, aluminium and zirconium in the catalyst composition, relative to the total mass of metals present in the catalyst composition, is calculated for the purposes of the present invention as the ratio of the mass of atoms of the one or more metals not selected from the group consisting of copper, aluminium and zirconium present in the catalyst composition divided by the total mass of metal atoms present in the catalyst composition (see the examples section for a calculation example).

Preferred variants or alternatives (e.g. of the copper present in the catalyst composition and/or of the substances of the carrier components and/or of the metals not selected from the group consisting of copper, aluminium and zirconium and/or preferred proportions or amounts of any of the foregoing) of the process according to the present invention as specified here above or below can preferably be combined and in case of their combination result in particularly preferred variants or alternatives of the process according to the invention.

Further preferred is a process according to the invention as defined herein (or a process according to the invention as described above or below as being preferred), wherein the catalyst composition comprises in addition to the copper:
- c2) a carrier component comprising one or more substances selected from the group consisting of aluminium, aluminium compounds, silicon and silicon compounds,
    - wherein preferably the or at least one substance is silicon or a silicon compound, wherein preferably the total amount of aluminium and silicon in the catalyst composition, relative to the total mass of copper present in the catalyst composition, is in the range of from 3.0 mass-% to 35.0 mass-%, more preferably of from 3.5 mass-% to 15.0 mass-%;

and/or (preferably "and")
- c3) one or more metals selected from the group consisting of manganese and zinc, wherein preferably the or at least one metal is manganese,
    - wherein preferably the total amount of manganese and zinc (or of manganese, in case only manganese is present and zinc is not present) in the catalyst composition, relative to the total mass of metals present in the catalyst composition, is in the range of from 0.5 mass-% to 35.0 mass-%, more preferably of from 0.75 mass-% to 30.0 mass-%;
    - and preferably
        - one or more metals selected from the group consisting of alkaline metals and alkaline earth metals, preferably selected from the group consisting of sodium, potassium, magnesium, calcium and barium,
        - wherein preferably the total amount of the one or more metals selected from the group consisting of alkaline metals and alkaline earth metals in the catalyst composition, relative to the total mass of metals present in the catalyst composition, is in the range of from 0.1 mass-% to 25.0 mass-%, more preferably of from 4.5 mass-% to 15.0 mass-%.

It has been found in own experiments that the use of a catalyst composition comprising (i) copper in the total amounts or preferred total amounts as specified above or below, (ii) the one or more of the preferred metals other than copper (as defined above or below, in particular comprising manganese and/or zinc, more in particular in the total amounts or preferred total amounts as specified above or below) and (iii) the preferred substances of the carrier component of the catalyst composition (as defined above or below, in particular comprising aluminium, aluminium compounds, silicon and/or silicon compounds, more in particular in the total amounts or preferred total amounts as specified above or below) in the process according to the present invention, results in a high selectivity of the hydrogenation process, a high conversion or conversion rate and is also associated with a particularly high yield of 1-(4-isobutylphenyl)ethanol, compared with similar processes known from the prior art.

Preferred is also a process according to the invention as defined herein (or a process according to the invention as described above or below as being preferred), wherein the catalyst composition comprises:
- c1) copper in a total amount in the range of from 60 mass-% to 95 mass-%, preferably of from 65 mass-% to 92.5 mass-%, relative to the total mass of metals present in the catalyst composition;
- c2) a carrier component comprising one or more substances selected from the group consisting of silicon and silicon compounds, wherein the total amount of silicon in the catalyst composition, relative to the total mass of copper present in the catalyst composition, is in the range of from 3.5 mass-% to 15.0 mass-%, preferably of from 5.0 mass-% to 15.0 mass-%;

and
- c3) manganese in a total amount in the range of from 0.5 mass-% to 20.0 mass-%, preferably of from 0.75 mass-% to 15.0 mass-%, relative to the total mass of metals present in the catalyst composition;
    - and preferably
        - one or more metals selected from the group consisting of sodium and calcium, wherein the total amount of the one or more metals selected from the group consisting of sodium and calcium in the catalyst composition, relative to the total mass of metals present in the catalyst composition, is in the range of from 4.5 mass-% to 15.0 mass-%, preferably of from 7.5 mass-% to 12.5 mass-%,
    - and wherein preferably
        - the added masses of components c1) and c3) present in the catalyst composition make up ≥95 mass-%, more preferably ≥98 mass-%, even more preferably the total mass, of metals (or metal atoms) present in the catalyst composition.

In the particularly preferred variant of the process according to the present invention as defined here before, it is further preferred that the added masses of copper atoms, manganese atoms, sodium atoms and calcium atoms present in the catalyst composition together make up ≥90 mass-%, preferably ≥95 mass-%, more preferably ≥98 mass-%, of the total mass of metal atoms present in the catalyst composition.

A further advantage of the process of the present invention is, that 1-(4-isobutylphenyl)ethanol can be produced in high yield and at high selectivity and conversion rates while the catalyst compositions used only comprise low amounts or are ideally free of undesired components as potentially environmentally harmful heavy metals, e.g. nickel or chromium, and/or of economically unfavorable noble metals, e.g. palladium or ruthenium.

Preferred is therefore a process according to the invention as defined herein (or a process according to the invention as described above or below as being preferred), wherein in the catalyst composition of step S3) the molar ratio of
- copper:nickel is >10, preferably >100, more preferably >1000;

and/or
- copper:chromium is >10, preferably >100, more preferably >1000;

and/or
copper: ruthenium is >10, preferably >100, more preferably >1000;
and/or
copper: palladium is >10, preferably >100, more preferably >1000;
and/or
copper: graphite carbon is >50, preferably >500, more preferably >5000;

Particularly preferred is a variant of the process according to the invention as defined herein (or a process according to the invention as described above or below as being preferred), wherein in the catalyst composition of step S3) the molar ratio of
copper:aluminium is >10, preferably >100, more preferably >1000;
and/or
copper:zinc is >10, preferably >100, more preferably >1000.

The molar ratio of copper relative to the other elements in the catalyst composition as defined above is calculated for the purposes of the present invention as the ratio of the molar amount of copper atoms present in the catalyst composition divided by the molar amount of atoms of the respective other element (e.g. nickel, chromium or ruthenium) present in the catalyst composition.

In the context of the present invention, one of the molar ratios of copper relative to another element as specified above can alone be present in a catalyst composition or applicable to the catalyst composition (i.e. only one or one single of said ratios is present or applies to a catalyst composition) or two or more of said molar ratios of copper relative to another element as specified above can be present in or applicable to the catalyst composition in the same catalyst composition.

The molar ratios of copper (atoms) relative to the (atoms of) other elements as specified above can be determined by methods known in the art. For the purposes of the present invention, the molar ratios of copper atoms relative to the atoms of other elements are preferably determined by X-ray Fluorescence Spectroscopy after (sample) fusion ("Röntgenfluoreszenzspektroskopie nach Schmelzaufschluss"), as is known in the art. Other suitable analytical methods for this same purpose which usually deliver the same or essentially the same results are Inductively Coupled Plasma Optical Emission Spectroscopy (ICP OES) after total digestion (of the sample) ("ICP OES nach Totalaufschluss") and atomic absorption spectroscopy (AAS) measurement. Where necessary, the catalyst composition can be isolated from the reaction mixture or the reactor by known methods and/or samples thereof can be prepared which are suitable for use in the relevant analytical method (preferably X-ray fluorescence spectroscopy after (sample) fusion) according to methods known in the art.

It has been found in own experiments that the process according to the present invention is robust enough to tolerate a certain degree, in particular ≤50 mass-%, preferably ≤30 mass-%, more preferably ≤10 mass-%—relative to the total mass of 1-(4-isobutylphenyl)ethanone and impurities—of impurities, preferably of organic impurities, to be present during step S3) without significantly impacting the favorable results of the process, in particular in terms of selectivity, conversion and product yield. Such impurities may e.g. be present in a starting compound 1-(4-isobutylphenyl)ethanone where said starting compound is provided or produced in technical grade or where 1-(4-isobutylphenyl)ethanone recycled from another process is used. Such robustness is another benefit of the present process.

In general, the 1-(4-isobutylphenyl)ethanone ("IBAP") used as starting material in the process of the present invention and which is suitable for this purpose may comprise low amounts, i.e. ≤10 mass-%, preferably ≤5 mass-%, more preferably ≤2 mass-%, relative to the total mass of the 1-(4-isobutylphenyl)ethanone used as starting material and the other organic and inorganic chemical compounds, of other organic or inorganic chemical compounds, e.g. acetic acid, acetates, fluorides and/or chlorides; oxygen-containing compounds, e.g. alcohols, ketones, aldehydes, esters, ethers and/or water; nitrogen-containing compounds, e.g. amines, amides, urea compounds, nitrates, nitrites and/or nitrosyl compounds; sulfur-containing compounds, e.g. thiols, thio ethers, sulfides, sulfates and/or sulfones. Typically, the 1-(4-isobutylphenyl)ethanone may comprise one or more of said other organic or inorganic chemical compounds in amounts of up to 200 ppm per compound.

The process according to the invention is favorably conducted as a liquid-phase hydrogenation process of a type generally known.

Preferred is therefore a process according to the invention as defined herein (or a process according to the invention as described above or below as being preferred), wherein (under the process conditions)
the 1-(4-isobutylphenyl)ethanone is present in the liquid phase for at least a part of the process or process time of step S3),
and/or
1-(4-isobutylphenyl)ethanone and/or 1-(4-isobutylphenyl)ethanol make up 90.0 vol.-%, preferably ≥92.0 vol.-%, of the liquid phase in step S3).

Preferably, 1-(4-isobutylphenyl)ethanone itself is present in the liquid phase under the reaction conditions rather than being present under the reaction conditions as solution of 1-(4-isobutylphenyl)ethanone in a liquid phase formed by another compound or mixture of compounds (e.g. as solid 1-(4-isobutylphenyl)ethanone, dissolved in a solvent).

Preferably, 1-(4-isobutylphenyl)ethanone and/or 1-(4-isobutylphenyl)ethanol make up 90.0 mass-%, more preferably ≥92.0 mass-%, of the liquid phase in step S3). It is preferred that only a low amount of solvents or other additives (other than the actual reactants or products of the process according to the invention present in step S3), or as present in the starting materials) are present in step S3). Preferably, solvents or other additives (other than the actual reactants or products of the process according to the invention present in step S3), or as present in the starting materials) make up ≤10 mass-%, more preferably ≤8 mass-% of the liquid phase in step S3) and even more preferably no such solvents are present in step S3). In a preferred alternative of the process according to the invention, only the starting compound 1-(4-isobutylphenyl)ethanone (in its actual degree of purity, preferably in a purity of ≥90 mass-% relative to the total mass of 1-(4-isobutylphenyl)ethanone and impurities), hydrogen and the catalyst composition (as defined in this text) are provided and/or are present at the start of step S3) (and—where applicable—in addition any impurities present in the 1-(4-isobutylphenyl)ethanone).

In the process according to the invention (step S3)), the hydrogen is preferably present as hydrogen gas or as a mixture of gases comprising hydrogen gas and one or more other gases which are compatible with the hydrogenation reaction and/or which are inert under the reaction conditions.

Examples for "other gases" which may be used in the process according to the invention in a mixture together with hydrogen gas are noble gases, specifically helium, neon, argon, krypton and/or xenon; nitrogen, carbon monoxide and/or carbon dioxide, preferably nitrogen. Gases comprising hydrogen may include, for example, reformer offgases, refinery gases, etc. These gases comprising hydrogen usually have a hydrogen content in the range of from 10 vol.-% to 100 vol.-%, preferably of from 50 vol.-% to 100 vol.-%.

A process according to the invention as defined herein is therefore preferred (or a process according to the invention as described above or below as being preferred), wherein the hydrogen in step S3) is present as hydrogen gas or (preferably) as a mixture of gases comprising hydrogen gas and one or more gases selected from the group consisting of helium, neon, argon, krypton, xenon, nitrogen, carbon monoxide, carbon dioxide and mixtures thereof. Preferably the hydrogen is present as a mixture of gases comprising hydrogen gas and nitrogen gas.

The process according to the present invention can be carried out at a wide range of reaction pressures. However, preferred ranges of reaction pressure which have been found to deliver particularly good results are defined here below.

Also preferred is a process according to the invention as defined herein (or a process according to the invention as described above or below as being preferred), wherein the reacting in step S3) is carried out at least for a part of the process or process time (of step S3)):
at a hydrogen pressure in the range of from 0.5 to 8.0 MPa, preferably of from 1.5 to 4.5 MPa and more preferably of from 2.5 to 4.25 MPa;
and/or
at a molar ratio of hydrogen to the 1-(4-isobutylphenyl) ethanone which is present at the start of step S3) in the range of from 1 to 20, preferably of from 1.01 to 10, more preferably of from 1.01 to 5.0 and yet more preferably of from 1.01 to 2.0;
and/or
at a temperature in the range of from 30° C. to 200° C., preferably of from 40° C. to 180° C., more preferably of from 40° C. to 150° C. and even more preferably of from 40° C. to 140° C.

Own experiments have shown that the best results of the process according to the invention in terms of combined optimized conversion and selectivity of the process are obtained in the temperature range as defined above in step S3).

The process according to the invention (in particular step S3) as defined above) can generally be carried out as a continuous operation or batch-wise. In a preferred variant, the process according to the invention is carried out as a continuous operation.

When the process according to the invention (in particular step S3) as defined above) is carried out batch-wise, it can be carried out, for example, in a stirred tank or a stirred autoclave, in a loop reactor, a jet loop reactor, a bubble column or in a fixed-bed reactor with a pumped circulation circuit. It is preferred that the batch-wise hydrogenation is carried out in a stirred tank or a stirred autoclave.

When the process according to the invention (in particular step S3) as defined above) is carried out as a continuous operation or in continuous mode, it is preferably carried out in a continuously operated stirred tank reactor, a continuously operated loop reactor, a continuously operated jet loop reactor, a continuously operated bubble column or a continuously operated fixed-bed reactor with a pumped circulation circuit and/or in a stirred tank cascade. Where the process according to the invention (in particular step S3) as defined above) is carried out as a continuous operation or in continuous mode, preferably two (or three) or more reactors are or can be used which can be serially or parallelly connected and in each case may or may not comprise a recycle loop. Said serially two (or three) or more serially connected reactors may comprise one or more main reactors, each comprising one or more recycle loops (as is known in the art) and one or more post-reactors, not comprising recycle loops. Usual, suitable or beneficial arrangements and/or orders of such main and post reactors (if present) relative to each other are known in the art. Said two (or three) or more serially connected reactors can be operated at the same reaction conditions or some or all of said two (or three) or more serially connected reactors can be operated at different reaction conditions. For example, said two (or three) or more serially connected reactors can be operated at the same reaction temperatures or they can be operated at different reaction temperatures.

In a reactor setup which comprises one or more recycle loops, a part of the material from the reactor outlet, comprising the reaction product from step S3) (also referred to as the "recycled material"), is recycled back to the reactor inlet where it is combined with the feed (i.e. the starting compounds being fed into step S3), in particular the compound 1-(4-isobutylphenyl)ethanone. Recycling a part of the product from a catalytic hydrogenation process back into the hydrogenation reactor in a "recycle loop" (see above) is generally known in the art. The mass ratio of the mass of the "recycled material" to the mass of the "feed" is known as the "recycle ratio".

In a preferred variant of the process of the present invention, the reactor inlet temperature (preferably the inlet temperature of at least one main reactor) is in the range of from 30° C. to 120° C., preferably in the range of from 40° C. to 100° C., and/or the reactor outlet temperature (preferably the outlet temperature of said at least one main reactor) is in the range of from 90° C. to 200° C., preferably in the range of from 100° C. to 180° C. and more preferably in the range of from 100° C. to 150° C. The temperature gradient which may occur between the reactor inlet and the reactor outlet of one particular reactor is e.g. resulting from the released reaction heat of the hydrogenation process.

It is preferable to carry out the process according to the invention (in particular step S3) as defined above) in trickle reactors or in flooded mode by the fixed-bed mode, for example according to WO 2008/015135 A1. The hydrogen may in these cases be passed over the catalyst composition either in co-current with the solution of the reactant to be hydrogenated (i.e. 1-(4-isobutylphenyl)ethanone), or in counter-current.

Useful apparatuses for carrying out a hydrogenation according to the process of the present invention over a fluidized catalyst bed and over a fixed catalyst bed are known from the prior art, for example from "Ullmanns Enzyklopädie der Technischen Chemie", 4th edition, volume 13, p. 135 ff., and also from P. N. Rylander, "Hydrogenation and Dehydrogenation" in Ullmann's Encyclopedia of Industrial Chemistry, 5th ed. on CD-ROM.

The process according to the invention (in particular step S3) as defined above) can also be carried out in suspension mode (applicable for both, continuous and batch mode). Useful reactors for carrying out the process according to the invention in suspension mode are known per se to those skilled in the art, for example stirred tanks, bubble columns, loop reactors and/or jet loop reactors. In accordance with the invention, a cascade of two or more serially connected suspension reactors may also be used, for example a stirred tank cascade or a bubble column cascade.

In order to attain complete conversion in the process according to the invention (in particular in step S3) as defined above), the hydrogenation discharge may be post-reacted. To this end, the hydrogenation discharge may, following the hydrogenation process, be passed through one or more downstream reactors in the gas phase or in the liquid phase in straight pass or by pumping in circulation. If liquid phase hydrogenation is concerned, the same reactor types as previously explained can be used (i.e. stirred tank reactor, loop reactor, jet loop reactor, bubble column or fixed-bed reactor with a pumped circulation circuit and/or in a stirred tank cascade). When a fixed-bed reactor is used, the reactor can be operated in trickle mode or in flooded mode. The reactor is packed with the catalyst composition and/or the pre-catalyst composition as defined above or below.

Preferred is a process according to the invention as defined herein (or a process according to the invention as described above or below as being preferred), wherein:
the reacting in step S3) is carried out continuously for at least a part of the process or process time (in step S3)), preferably for the full process or process time (in step S3)),
preferably
in one or more fixed-bed reactors,
and/or
in two or more serially connected reactors comprising one or more main reactors, each comprising one or more recycle loops or one combined recycle loop, and one or more post-reactors, not comprising recycle loops,
wherein preferably the recycle ratio in the one or more recycle loops is in the range of from 0.1 to 20, preferably of from 0.5 to 10 and more preferably of from 0.5 to 8;
and/or (preferably "and")
the catalyst composition is or comprises, preferably is, a fixed-bed catalyst or fixed-bed catalyst composition,
and/or
the catalyst load is in the range of from 0.1 kg [1-(4-isobutylphenyl)ethanone]/(kg catalyst composition*h) to 5.0 kg [1-(4-isobutylphenyl)ethanone/(kg catalyst composition*h), preferably of from 0.5 kg [1-(4-isobutylphenyl)ethanone]/(kg catalyst composition*h) to 3.0 kg [1-(4-isobutylphenyl)ethanone]/(kg catalyst composition*h), more preferably of from 1.0 kg [1-(4-isobutylphenyl)ethanone]/(kg catalyst composition*h) to 2.5 kg [1-(4-isobutylphenyl)ethanone]/(kg catalyst composition*h),
where the kg [1-(4-isobutylphenyl)ethanone] is the total amount of 1-(4-isobutylphenyl)ethanone present at the start of the reaction (in step S3);
and/or
1-(4-isobutylphenyl)ethanone is continuously fed into or provided to reaction step S3) in an amount of 500 t/h, preferably of 350 t/h and more preferably of 150 t/h.

In the context of the present invention, the term "catalyst load" as defined above preferably means the mass ratio of the total mass of 1-(4-isobutylphenyl)ethanone present at the start of the reaction in step S3) (preferably in the reactor wherein the hydrogenation process is carried out) relative to the total mass of catalyst composition present at the start of the reaction in step S3) (preferably in the reactor wherein the hydrogenation process is carried out). The "start of the reaction in step S3)" preferably means the point in time where in step S3) the reaction time t=0.

In continuous mode the term "catalyst load" preferably means the ratio of the total mass flow of 1-(4-isobutylphenyl)ethanone present at the inlet of the reactor (preferably the reactor wherein the hydrogenation process is carried out) relative to the total mass of catalyst composition which is present at the start of the reaction in step S3) (preferably in the reactor wherein the hydrogenation process is carried out).

It was observed in own experiments that the performance of a process (as defined above or below) could differ depending on the process being carried out either in continuous mode (e.g. in a fixed-bed reactor) or in batch mode for processes using equal catalyst compositions in step S3).

It could also be shown that conducting the process according to the invention, preferably a continuous process, with a catalyst load in the range (particularly in the preferred ranges) as defined above brought about the best results in terms of conversion to the main product (1-(4-isobutylphenyl)ethanol). At catalyst load rates below 0.1 kg [1-(4-isobutylphenyl)ethanone]/(kg catalyst composition*h), preferably below 0.5 kg [1-(4-isobutylphenyl)ethanone]/(kg catalyst composition*h), more preferably below 1.0 kg [1-(4-isobutylphenyl)ethanone]/(kg catalyst composition*h), (product) selectivity did not reach its maximum value. At catalyst load rates above 5.0 kg [1-(4-isobutylphenyl)ethanone]/(kg catalyst composition*h), preferably above 3.0 kg [1-(4-isobutylphenyl)ethanone]/(kg catalyst composition*h), more preferably above 2.5 kg [1-(4-isobutylphenyl)ethanone]/(kg catalyst composition*h), product conversion decreased from its maximum value.

Where the reaction according to the invention is carried out in batch mode or in semi-batch mode, the catalyst composition is preferably used in a total amount in the range of 0.01 mass-% to 10.0 mass-%, preferably of from 0.1 mass-% to 5.0 mass-%, more preferably of from 0.5 mass-% to 3.0 mass-%, relative to the total mass of 1-(4-isobutylphenyl)ethanone used at the start of step S3).

A process according to the invention as defined herein is preferred (or a process according to the invention as described above or below as being preferred), further comprising the following steps (to be carried out in addition and) before step S3):
S1) providing or preparing a pre-catalyst composition comprising a mixture of oxides of copper and oxides of one or more metals other than copper,
wherein the pre-catalyst composition comprises the oxides of copper in a total amount in the range of from 30 mass-% to 90 mass-%, preferably of from 50 mass-% to 85 mass-%, more preferably of from 55 mass-% to 80 mass-% and even more preferably of from 70 mass-% to 80 mass-%, relative to the total mass of the pre-catalyst composition;
and
S2) reacting the pre-catalyst composition from step S1) with hydrogen, preferably at a temperature in the range of from 120° C. to 230° C., more preferably of from 160° C. to 230° C.,
so that the catalyst composition comprising copper and one or more metals other than copper used in step S3) (as defined above) results.

A process according to the present invention is preferred, wherein in step S1) the oxides of copper comprise CuO and/or $Cu_2O$, wherein preferably CuO makes up ≥90 mass-%, more preferably ≥95 mass-%, of the oxides of copper in step S1). In a preferred alternative of the process of the present invention, CuO makes up ≥99.9 mass-% of the oxides of copper in step S1).

The total amount of copper atoms and/or of atoms of one or more metals other than copper present in the pre-catalyst composition in step S1) (and/or in step S2)) of the process according to the invention can be quantitatively determined by methods known in the art. In the context of the present invention, the total amount of oxides of copper and/or of oxides of one or more metals other than copper present in the pre-catalyst composition in step S1) (and/or in step S2)) of the process according to the invention, relative to the total mass of the pre-catalyst composition is preferably determined by X-ray Fluorescence Spectroscopy after (sample) fusion ("Röntgenfluoreszenzspektroskopie nach Schmelzaufschluss"), as is known in the art. Other suitable analytical methods for this same purpose which usually deliver the same or essentially the same results are Inductively Coupled Plasma Optical Emission Spectroscopy (ICP OES) after total digestion (of the sample) ("ICP OES nach Totalaufschluss") and Atomic Absorption Spectroscopy (AAS) measurement. Where necessary, the pre-catalyst composition can be isolated from the reaction mixture and/or from the reactor and/or from its formulation and/or samples can be prepared of the pre-catalyst composition which are suitable for use in the analytical method (preferably X-ray fluorescence spectroscopy after (sample) fusion) according to methods known in the art.

The oxides of one or more metals other than copper or the preferred oxides of one or more metals other than copper present in the pre-catalyst composition of step S1) and/or of step S2) (preferably their total amounts) preferably correspond to the one or more metals other than copper or preferred metals other than copper (or the respective atoms of one or more metals other than copper) present in the catalyst composition of step S3), as defined above. Likewise, the combinations of oxides of metals other than copper and the preferred combinations of oxides of metals other than copper present in the pre-catalyst composition of step S1) and/or of step S2) (preferably their total amounts, as defined below) preferably correspond to the combinations of metals other than copper and the preferred combinations of metals other than copper present in the catalyst composition of step S3), as defined above.

The reacting of the pre-catalyst composition in step S2) corresponds to "activating" the pre-catalyst composition, comprising reducing oxides of copper (in particular CuO) present in the pre-catalyst composition, as is generally known in the art. Said activation step S2) can in principle be performed at the same time and under the same conditions as step S3), however, this is not preferred.

In preferred variants of the process of the present invention, the catalyst composition used in step S3) of the process according to the invention is prepared from the pre-catalyst composition used in step S2) of the process according to the invention by a reduction process, as explained above. The composition, constituents, preferred constituents, ratios of constituents and preferred ratios of constituents as defined above for the catalyst composition of the process according to the invention (see step S3) above) therefore preferably also apply mutatis mutandis for the pre-catalyst composition of the process according to the invention (see steps S1) and S2).

For example, the total (molar) amount or proportion of copper (or copper atoms) present in said catalyst composition (used in step S3)) preferably corresponds to the respective total (molar) amount or proportion of copper (or copper atoms) present in said pre-catalyst composition (used in step S2) and/or provided or prepared in step S1)) since it can be assumed that the molar amount of copper atoms present in said pre-catalyst composition does not change relative to the molar amount of copper atoms present in said catalyst composition prepared from said pre-catalyst composition under the reaction conditions applied (and defined in this text). Similarly, the molar amounts of metals other than copper present in a pre-catalyst composition (in particular present therein as oxides of one or more metals other than copper) do not change relative to the molar amounts of metals other than copper present in a respective catalyst composition prepared from said pre-catalyst composition under the reaction conditions applied (and defined in this text). And similarly, the molar amounts of silicon (atoms) and carbon (i.e. carbon atoms present as graphite) present in a pre-catalyst composition do not change relative to the molar amounts of silicon (atoms) and carbon (i.e. carbon atoms present as graphite) present in a respective catalyst composition prepared from said pre-catalyst composition under the reaction conditions applied (and defined in this text).

Preferred is thus a process according to the invention as defined herein (or a process according to the invention as described above or below as being preferred), comprising the steps S1) providing or preparing a pre-catalyst composition comprising a mixture of oxides of copper and oxides of one or more metals other than copper,
wherein the pre-catalyst composition comprises the oxides of copper in a total amount in the range of from 30 mass-% to 90 mass-%, preferably of from 50 mass-% to 85 mass-%, more preferably of from 55 mass-% to 80 mass-% and even more preferably of from 70 mass-% to 80 mass-%, relative to the total mass of the pre-catalyst composition;

S2) reacting the pre-catalyst composition from step S1) with hydrogen, preferably at a temperature in the range of from 120° C. to 230° C., more preferably of from 160° C. to 230° C.,
so that the catalyst composition comprising copper and one or more metals other than copper used in step S3) results, and S3) reacting 1-(4-isobutylphenyl)ethanone with hydrogen in the presence of the catalyst composition comprising copper and one or more metals other than copper from step S2),
wherein preferably the catalyst composition from step S2) comprises the copper in a total amount in the range of from 30 mass-% to 98 mass-%, preferably of from 45 mass-% to 98 mass-%, more preferably of from 60 mass-% to 95 mass-% and even more preferably of from 65 mass-% to 92.5 mass-%, relative to the total mass of metals present in the catalyst composition.

The preferred temperature range in step S2) of the process according to the invention (as defined above) is preferably combined with the preferred pre-catalyst compositions as defined in the present text.

Preferred is also a process according to the invention as defined herein (or a process according to the invention as described above or below as being preferred), wherein
the pre-catalyst composition is present for at least a part of the process or process time, preferably of step S1) and/or step S2), as a formulation of solid particles, preferably selected from the group consisting of extrudates, tablets, pellets, strands, stars, powders, granules, granulates and mixtures thereof; preferably the pre-catalyst is present for at least a part of the process or process time as a formulation of solid particles selected from the group consisting of extrudates, preferably trilobed extrudates and extrudates of similar shapes; and tablets;

and/or the reacting in step S2) is carried out for at least a part of the reaction or reaction time (of step S2)) in the presence of a gaseous atmosphere comprising hydrogen gas and one or more other gases which are inert under the reaction conditions.

Where the pre-catalyst composition is present for at least a part of the process or process time as a formulation of solid particles (as defined above), preferably as one or more extrudates (more preferably as one or more trilobed extrudates) and/or as one or more tablets, the mean particle size of said solid particles is preferably ≤7.5 mm, more preferably 5.0 mm and even more preferably ≤3.0 mm.

Where the pre-catalyst composition is used as or is present in the process of the present invention for at least a part of the process or process time as a formulation of solid extrudates, preferably as solid trilobed extrudates, the mean diameter of said solid extrudates (preferably of said solid trilobed extrudates) is preferably ≤7.5 mm, more preferably ≤5.0 mm and even more preferably ≤3.0 mm. In a preferred variant of the process of the present invention, the mean diameter of said solid extrudates (preferably of said solid trilobed extrudates) is in the range of from 0.5 mm to 7.5 mm, more preferably of from 0.5 mm to 5.0 mm and even more preferably of from 0.5 mm to 3.0 mm.

The mean length of said solid extrudates (preferably of said solid trilobed extrudates) is preferably in the range of from 0.01 mm to 250 mm, more preferably of from 0.05 mm to 150 mm and yet more preferably of from 0.01 to 100 mm. In certain preferred alternatives of the process of the present invention, the mean particle size of said solid particles and/or the mean diameter of said solid extrudates (preferably of said solid trilobed extrudates) is ≤2.0 mm. Preferably, the mean particle size of said solid particles and/or the mean diameter of said solid extrudates (preferably of said solid trilobed extrudates) is in the range of from 0.8 to 7.5 mm, more preferably of from 1.0 to 5.0 mm and even more preferred of ≥1.0 to ≤3.5 mm. In a particularly preferred variant of the process of the present invention, the mean particle size of said solid particles and/or the mean diameter of said solid extrudates (preferably of said solid trilobed extrudates) is in the range of ≥1.0 to ≤2.0 mm.

Where the pre-catalyst composition is present for at least a part of the process or process time as a formulation of solid particles (as explained above), the (macroscopic) shape of said formulation of solid particles and/or their mean particle size and/or their mean diameter and/or their mean length does usually not significantly change in any of steps S1), S2) and S3).

Preferred is therefore also a process according to the invention as defined herein (or a process according to the invention as described above or below as being preferred), wherein the catalyst composition is present for at least a part of the process or process time, preferably of step S3), as a formulation of solid particles, preferably selected from the group consisting of extrudates, tablets, pellets, strands, stars, powders, granules, granulates and mixtures thereof. Preferably the pre-catalyst is present for at least a part of the process or process time as one or more extrudates, more preferably as one or more trilobed extrudates and/or extrudates of similar shapes.

In the context of the present invention, the mean particle size of the solid particles and/or the mean diameter of the solid extrudates of the pre-catalyst composition (as defined above) and/or of the catalyst composition is preferably determined by dynamic image analysis, preferably using a Camsizer™ dynamic image analyzer.

The pre-catalyst composition as used in step S1) and/or step S2) of the process according to the invention may further comprise (in addition to the mixture of oxides of copper, the oxides of one or more metals other than copper and—where applicable—a carrier comprising one or more substances which are not oxides of metals, as explained below) additional constituents compatible with the hydrogenation process according to the invention (and/or compatible with the hydrogenation process after steps S1) and/or S2) have been carried out), e.g. catalytically inactive materials, clay materials (as defined below), fillers, binders and/or extrusion aids (as defined below). Such additional constituents, if present, are preferably only present in said pre-catalyst composition in a total amount of ≤10 mass-%, more preferably of ≤5 mass-% and even more preferably of ≤2 mass-%, of the total mass of the pre-catalyst composition. Preferred is, however, a process according to the invention as defined herein (or a process according to the invention as described above or below as being preferred), wherein the mixture of oxides of copper and oxides of one or more metals other than copper makes up ≥50 mass-%, preferably ≥70 mass-%, more preferably ≥75 mass-% and even more preferably ≥80 mass-%, of the total mass of the pre-catalyst composition.

A combination of different pre-catalyst compositions as defined in this text can also be used in the process according to the present invention (in steps S1) and/or S2)), but this alternative is not preferred.

In the process according to the invention, step S2), the hydrogen is preferably present as hydrogen gas or as a mixture of gases comprising hydrogen gas and one or more other gases which are compatible with the hydrogenation reaction and/or are inert under the reaction conditions. Examples for "other gases" which may be used in the process according to the invention in a mixture together with hydrogen gas are noble gases, specifically helium, neon, argon, krypton and/or xenon; nitrogen, carbon monoxide and/or carbon dioxide. Gases comprising hydrogen may include, for example, reformer offgases, refinery gases, etc. as explained above.

A process according to the invention as defined herein is therefore preferred (or a process according to the invention as described above or below as being preferred), wherein the hydrogen in step S2) is present as hydrogen gas or as a mixture of gases comprising hydrogen gas and one or more gases selected from the group consisting of helium, neon, argon, krypton, xenon, nitrogen, carbon monoxide, carbon dioxide and mixtures thereof.

Preferred is also a process according to the present invention as defined herein (or a process according to the invention as described above or below as being preferred), wherein the pre-catalyst composition comprises in addition to the oxides of copper:

p2) a carrier comprising one or more substances selected from the group consisting of carbon (graphite) and oxides of aluminium, silicon and zirconium,
wherein preferably the total amount of carbon and oxides of aluminium, silicon and zirconium in the pre-catalyst composition, relative to the total mass of the pre-catalyst composition, is in the range of from 2.0 mass-% to 50.0 mass-%, more preferably of from 3.0 mass-% to 35.0 mass-% and yet more preferably of from 3.5 mass-% to 20.0 mass-%;

and/or (preferably "and")
p3) oxides of one or more metals not selected from the group consisting of copper, aluminium and zirconium, wherein preferably the total amount of the oxides of one or more metals not selected from the group consisting of copper, aluminium and zirconium in the pre-catalyst composition, relative to the total mass of the pre-catalyst composition, is in the range of from 0.1 mass-% to 55.0 mass-%, preferably of from 2.5 mass-% to 35.0 mass-% and yet more preferably of from 5.0 mass-% to 25.0 mass-%.

Preferred is also a process according to the invention as defined herein (or a process according to the invention as described above or below as being preferred), wherein (in the pre-catalyst composition as defined above) the added masses of:
the oxides of copper,
the one or more substances selected from the group consisting of carbon (graphite) and oxides of aluminium, silicon and zirconium (component p2))
and
the oxides of one or more metals not selected from the group consisting of copper, aluminium and zirconium (component p3)), make up ≥75 mass-%, preferably ≥90 mass-%, more preferably ≥95 mass-% and even more preferably ≥98 mass-%, of the total mass of the pre-catalyst composition.

Further preferred in this regard is a process according to the invention as defined herein (or a process according to the invention as described above or below as being preferred), wherein the pre-catalyst composition comprises in addition to the oxides of copper:
p2) a carrier comprising one or more substances selected from the group consisting of oxides of aluminium and silicon,
wherein preferably the total amount of oxides of aluminium and silicon in the pre-catalyst composition, relative to the total mass of the pre-catalyst composition, is in the range of from 2.0 mass-% to 40.0 mass-%, more preferably of from 3.0 mass-% to 35.0 mass-% and yet more preferably of from 10.0 mass-% to 20.0 mass-%;
and/or
p3) oxides of one or more metals selected from the group consisting of manganese and zinc, wherein preferably the or at least one metal is manganese,
wherein preferably the total amount of the oxides of one or more metals selected from the group consisting of manganese and zinc in the pre-catalyst composition, relative to the total mass of the pre-catalyst composition, is in the range of from 0.5 mass-% to 30.0 mass-%, preferably of from 0.75 mass-% to 27.5 mass-% and yet more preferably of from 1.0 mass-% to 25.0 mass-%,
and preferably
oxides of one or more metals selected from the group consisting of alkaline metals and alkaline earth metals, preferably selected from the group consisting of sodium, potassium, magnesium, calcium and barium,
wherein preferably the total amount of the oxides of one or more metals selected from the group consisting of alkaline metals and alkaline earth metals in the catalyst composition, relative to the total mass of the pre-catalyst composition, is in the range of from 0.1 mass-% to 35.0 mass-%, preferably of from 5.0 mass-% to 25.0 mass-% and more preferably of from 5.0 mass-% to 15.0 mass-%.

Still further preferred in this regard is a process according to the invention as defined herein (or a process according to the invention as described above or below as being preferred), wherein the pre-catalyst composition comprises:
p1) oxides of copper in a total amount in the range of from 50 mass-% to 85 mass-%, preferably of from 55 mass-% to 80 mass-% and more preferably of from 70 mass-% to 80 mass-%, relative to the total mass of the pre-catalyst composition;
p2) a carrier comprising oxides of silicon, preferably $SiO_2$, wherein the total amount of oxides of silicon in the pre-catalyst composition, relative to the total mass of the pre-catalyst composition, is in the range of from 3.0 mass-% to 35.0 mass-%, preferably of from 10.0 mass-% to 20.0 mass-%;
and
p3) oxides of manganese, preferably $MnO_2$, wherein the total amount of the oxides of manganese in the pre-catalyst composition, relative to the total mass of the pre-catalyst composition, is in the range of from 0.5 mass-% to 25.0 mass-%, preferably of from 1.0 mass-% to 15.0 mass-% and more preferably of from 1.0 mass-% to 5.0 mass-%,
and preferably
oxides of one or more metals selected from the group consisting of sodium and calcium, wherein the total amount of the oxides of one or more metals selected from the group consisting of sodium and calcium, relative to the total mass of the pre-catalyst composition, is in the range of from 5.0 mass-% to 25.0 mass-%, preferably of from 5.0 mass-% to 15.0 mass-%.

In a preferred variant of the process of the present invention, the added masses of the components p1), p2) and p3) (as defined here above) make up ≥90 mass-%, preferably 95 mass-%, more preferably ≥98 mass-%, of the total mass of the pre-catalyst composition. In a particularly preferred variant of the process of the present invention, the added masses of the components p1), p2) and p3) (as defined here above) make up the total mass of the pre-catalyst composition (i.e. the pre-catalyst composition consists in this preferred variant of the components p1), p2) and p3) in the amounts or preferred amounts as specified here above).

Preferred is also a process according to the invention as defined herein (or a process according to the invention as described above or below as being preferred), wherein in the pre-catalyst composition of step S1) and/or of step S2) the molar ratio of:
copper:nickel is >10, preferably >100, more preferably >1000; even more preferably the pre-catalyst composition does not comprise nickel;
and/or
copper:chromium is >10, preferably >100, more preferably >1000; even more preferably the pre-catalyst composition does not comprise chromium;
and/or
copper: ruthenium is >10, preferably >100, more preferably >1000; even more preferably the pre-catalyst composition does not comprise ruthenium;
and/or
copper: palladium is >10, preferably >100, more preferably >1000; even more preferably the pre-catalyst composition does not comprise palladium;
and/or copper: carbon (graphite) is >50, preferably >500, more preferably >5000; even more preferably the pre-catalyst composition does not comprise graphite.

Particularly preferred is a variant of the process according to the invention as defined herein (or a process according to the invention as described above or below as being preferred), wherein in the pre-catalyst composition of step S1) and/or of step S2) the molar ratio of copper:aluminium is >10, preferably >100, more preferably >1000; even more preferably the pre-catalyst composition does not comprise aluminium;

and/or (preferably "and")

copper:zinc is >10, preferably >100, more preferably >1000; even more preferably the pre-catalyst composition does not comprise zinc The molar ratio of copper relative to the other elements in the pre-catalyst composition as defined above is calculated for the purposes of the present invention as the ratio of the molar amount of copper atoms present in the pre-catalyst composition divided by the molar amount of atoms of the respective other element (e.g. nickel, chromium or ruthenium) present in the catalyst composition.

In the context of the present invention, the molar ratios of the copper atoms relative to the atoms of other elements as specified above can alone be present in or applicable to the pre-catalyst composition (i.e. only one or one single of said ratios is present or applies to a catalyst composition) or two or more of said molar ratios of the copper atoms relative to the atoms of other elements as specified above can be present in or applicable to the pre-catalyst composition.

The molar ratios of the copper atoms present in the pre-catalyst composition relative to the atoms of other elements as specified above can be determined by methods known in the art. For the purposes of the present invention, the molar ratios of copper atoms relative to the atoms of other elements present in the pre-catalyst composition are preferably determined by X-ray Fluorescence Spectroscopy after (sample) fusion ("Röntgenfluoreszenzspektroskopie nach Schmelzaufschluss"), as is known in the art. Other suitable analytical methods for this same purpose which usually deliver the same or essentially the same results are Inductively Coupled Plasma Optical Emission Spectroscopy (ICP OES) after total digestion (of the sample) ("ICP OES nach Totalaufschluss") and Atomic Absorption Spectroscopy (AAS) measurement. Where necessary, the pre-catalyst composition can be isolated from the reaction mixture and/or from the reactor and/or from its formulation and/or samples can be prepared of the pre-catalyst composition which are suitable for use in the relevant analytical method (preferably X-ray fluorescence spectroscopy after (sample) fusion) according to methods known in the art.

Where the reaction according to the invention is carried out in batch mode or in semi-batch mode, the pre-catalyst composition is preferably used in a total amount in the range of 0.01 mass-% to 10.0 mass-%, preferably of from 0.1 mass-% to 5.0 mass-%, more preferably of from 0.5 mass-% to 3.0 mass-%, relative to the total mass of 1-(4-isobutylphenyl)ethanone used at the start of step S3).

Preferred is also a process according to the invention as defined herein (or a process according to the invention as described above or below as being preferred), wherein the reacting in step S3) is carried out continuously for at least a part of the process or process time, preferably in one or more fixed-bed reactors;

and/or (preferably "and")

the pre-catalyst composition is used (at the start of step S2), i.e. is prepared or provided in step S1)) in a mass ratio (also referred to as "pre-catalyst load" in the following) in the range of from 0.1 kg [1-(4-isobutylphenyl)ethanone]/(kg pre-catalyst composition*h) to 5.0 kg [1-(4-isobutylphenyl)ethanone]/(kg pre-catalyst composition*h), preferably of from 0.5 kg [1-(4-isobutylphenyl)ethanone]/(kg pre-catalyst composition*h) to 3.0 kg [1-(4-isobutylphenyl)ethanone]/ (kg pre-catalyst composition*h), more preferably of from 1.0 kg [1-(4-isobutylphenyl)ethanone]/(kg pre-catalyst composition*h) to 2.5 kg [1-(4-isobutylphenyl) ethanone]/(kg pre-catalyst composition*h), where the kg [1-(4-isobutylphenyl)ethanone] is the total amount (i.e. mass) of 1-(4-isobutylphenyl)ethanone present at the start of the reaction in step S3), and/or the pre-catalyst composition is used or provided in a fixed-bed.

In the context of the present invention, the term "pre-catalyst load" as defined above preferably means the mass ratio of the total mass of 1-(4-isobutylphenyl)ethanone present at the start of the reaction in step S3) (i.e. where in step S3) the reaction time t=0 and/or where in the continuous mode the kg [1-(4-isobutylphenyl)ethanone] is the total amount of 1-(4-isobutylphenyl)ethanone present at the inlet of the reactor) relative to the total mass of pre-catalyst composition provided or prepared in step S1) of the process of the present invention. The total mass of pre-catalyst composition provided or prepared in step S1) is preferably the same as the total mass of pre-catalyst composition used at the start of step S2) of the process of the present invention.

The total amounts (masses) of pre-catalyst composition used in step S2) are very similar to the total amounts (masses) of catalyst composition used in step S3) as defined above. Although it can be assumed that (i) the catalyst composition used in step S3) which results from "activation" of a corresponding pre-catalyst composition in step S2) and (ii) said pre-catalyst composition do not have identical masses, any such mass difference occurring in practice is not regarded as relevant for the purpose of the present invention, specifically for the preferred process variant as defined here above. For the same reason, the values provided for the "catalyst load" (as defined above) and for the "pre-catalyst load" (as defined above) are very similar or identical.

The pre-catalyst compositions as defined in this text (i.e. the pre-catalysts which can be used in steps S1) and/or S2) of the process according to the invention) are known per se and/or can be prepared according to processes known in the art and/or are commercially available. E.g. the pre-catalyst compositions PCC1a, PCC1b, PCC2, PCC3, PCC4, PCC5, PCC6 and PCC7 (see the examples section below for details) are generally suitable as pre-catalyst compositions for the process according to the present invention and are commercially available, e.g. from BASF SE, Germany.

The present invention also relates to the use of a composition comprising copper and one or more metals other than copper, wherein the composition comprises the copper in a total amount in the range of from 30 mass-% to 98 mass-%, preferably of from 45 mass-% to 98 mass-%, more preferably of from 60 mass-% to 95 mass-%, relative to the total mass of metals present in the composition, and/or a pre-composition comprising a mixture of oxides of copper and oxides of one or more metals other than copper, wherein the pre-composition comprises the oxides of copper in a total amount in the range of from 30 mass-% to 90 mass-%, preferably of from 50 mass-% to 85 mass-% and more preferably of from 50 mass-% to 80 mass-%, relative to the total mass of the pre-composition,
in a catalytic hydrogenation process, preferably a selective hydrogenation process, for producing 1-(4-isobutylphenyl) ethanol from 1-(4-isobutylphenyl)ethanone,
preferably in a process according to the invention as defined herein (or a process according to the invention as described in the present text as being preferred).

All aspects of the present invention discussed herein in the context of the process according to the invention (or a process according to the invention as described in the present text as being preferred) apply mutatis mutandis to the use according to the invention, as defined here above and below, and vice versa.

Preferred is a use according to the invention as defined herein (or a use according to the invention as described in this text as being preferred), wherein
the catalytic hydrogenation process, preferably step S3), comprises a continuous hydrogenation process
and/or
is at least partly performed as a continuous hydrogenation process,
and/or (preferably "and")
the composition is or comprises a fixed-bed catalyst or fixed-bed catalyst composition and/or the pre-composition is used or provided in a fixed-bed.

Pre-catalyst compositions which are suitable for use in the process according to the present invention or in a preferred process according to the present invention (as defined above; in particular comprising pre-catalyst compositions PCC1a and PCC1b) can e.g. be manufactured by a method or process as described below:

The manufacturing method or process includes mixing a copper oxide and a clay material to obtain a dry material mixture; combining the dry material mixture with an aqueous acid-stabilized silica solution, a caustic material, and water to obtain a wet material mixture; and calcining the wet material mixture at a temperature, and for a time, sufficient to cure form a calcined hydrogenation pre-catalyst composition; wherein: the calcined hydrogenation pre-catalyst composition has a Brunauer-Emmett-Teller ("BET") surface area of ≥45 $m^2/g$; and the acid-stabilized silica solution has a pH of ≤3.5.

The dry material mixture may also include a clay material. Preferred clay materials comprise alumino-silicate clays such as attapulgites, sepiolites, serpentines, kaolinites, palygorskite, calcium montmorillonites and mixtures thereof. In a preferred variant according to the present invention, the clay material is or comprises an aluminosilicate attapulgite clay. For the purposes of the present invention, the term "attapulgite" is used to mean chain lattice type clay minerals, encompassing minerals and mineral groups variously referred to in the literature as "attapulgite," "palygorskite," "sepiolite," and "hormite." Typically, the clays or clay materials suitable for use in the instant invention contain a major amount of attapulgite. As used herein, "major amount" shall mean and refer to a component which is present in the largest amount of any of the components present.

Said manufacturing method or process may further include mixing a transition metal component into the dry material mixture. For example, in preferred variants, the transition metal component comprises one or more components selected from the group consisting of manganese, zinc, nickel, cobalt, iron and mixtures of two or more thereof. The transition metal component may be used in the form of a transition metal carbonate. In preferred variants according to the present invention, the transition metal component is selected from the group consisting of manganese and zinc. For example, in preferred variant of the method or process for the purpose of the present invention, the transition metal component is or comprises manganese carbonate.

Said manufacturing method or process may further include mixing an alkaline earth metal component. The alkaline earth metal component may be an alkaline earth metal hydroxide or an alkaline earth metal carbonate where the alkaline earth metal is selected from the group consisting of magnesium (Mg), calcium (Ca), strontium (Sr), barium (Ba), and combinations thereof. For example, in preferred variants for the purpose of the present invention, the alkaline earth metal component may be a calcium component. In a preferred variant of the method or process for the purpose of the present invention, the alkaline earth metal component is or comprises calcium hydroxide. In preferred variants, the alkaline earth metal component is used for the purposes of the present invention in particulate (e.g. powder) form or in an aqueous composition, preferably an aqueous solution comprising the alkaline earth metal component.

Said manufacturing method or process may further include mixing one or more binders, extrusion aids, or a combination thereof in to the dry material mixture. Suitable binders or extrusion aids are preferably selected from the group consisting of a polymeric polysaccharide, hydroxypropyl methyl cellulose, hydroxyethyl methyl cellulose, or a mixture of two or more thereof. For example, in preferred variants for the purpose of the present invention, the binder or extrusion aid may be selected from a commercially available binder or extrusion aid, including but not limited to, Zusoplast®, Methocel®, Walocel®, or a mixture thereof.

Said manufacturing method or process also includes combining the dry material mixture with an aqueous acid-stabilized silica solution component, a caustic material, and water. In preferred variants, the aqueous acid-stabilized silica solution may have a pH of ≤3.5. For example, in preferred variants for the purpose of the present invention, the aqueous acid-stabilized solution has a pH of ≤3.5, ≤3.3, ≤2.9, ≤2.7, ≤2.5, or ≤2.3. A preferred silica sol that is an acid-stabilized silica solution is sold under the trade name Levasil® CA320 DH having a pH from about 2.3 to about 3.3, a specific surface area of 200 $m^2/g$, a density of about 1.2 g/mL, a dynamic viscosity of about 7 cP (about 0.01 Pa*s), and about 34 mass-% silica (as $SiO_2$).

In said manufacturing method or process, the caustic material preferably is or includes an alkali metal compound. The alkali metal compound is preferably selected from the group consisting of an alkali metal hydroxide and an alkali metal carbonate. The alkali metal is preferably selected from the group consisting of sodium (Na), potassium (K), rubidium (Rb), cesium (Cs), and combinations thereof. For example, in preferred variants for the purpose of the present invention, the alkali metal compound is or comprises an alkali metal hydroxide, preferably sodium hydroxide.

Upon combining the dry material mixture with the aqueous acid-stabilized silica, caustic material, and water, the resultant wet material mixture usually undergoes an exothermic reaction. Without wishing to be bound by theory, in an exemplary variant, an exothermic reaction between $Ca(OH)_2$, NaOH, and $SiO_2$ may occur during the drying step to cure the wet material matrix. This exothermic reaction is assumed to be represented by the following chemical equation:

$$Ca(OH)_2 + 2NaOH + 2SiO_2 \rightarrow CaSiO_3 + Na_2SiO_3 + 2H_2O.$$

Said manufacturing method or process may further include removing at least some of the water from the wet material mixture prior to calcining (see below for the calcining step). For example, in preferred variants for the purpose of the present invention, the removing may include drying the wet material mixture. In preferred variants for the purpose of the present invention, the removing may be conducted at a temperature in the range of from 40° C. to 150° C. For example, in preferred variants for the purpose of the present invention, the removing may occur at a temperature of about 40° C., about 50° C., about 60° C., about 70° C., about 80° C., about 90° C., about 100° C., about 110° C., about 120° C., about 130° C., about 140° C., about 150° C., or any range including and/or in between any two of the preceding values. For example, in preferred variants for the purpose of the present invention, the removing may occur at a temperature in the range of from 40° C. to 80° C., preferably of from 45° C. to 65° C. and more preferably of from 50° C. to 60° C., or any range including and/or in between any two of the preceding values.

In preferred variants for the purpose of the present invention, the method may further include extruding or tableting the wet material mixture prior to calcining. For example, in preferred variants for the purpose of the present invention, the wet material mixture may be extruded or tableted in sizes (of the pre-catalyst compositions) which are suitable for the process according to the present invention, including e.g. sizes of 1/8" by 1/8", 3/16" by 3/16", 1/4" by 1/4", 3/16" by 1/4", 1/4" by 1/16", or 1/8" by 1/16". Extruding or tableting may be facilitated or supported by the presence in the wet material of a binder material, extrusion aid and/or one or more substances which are capable of acting as inorganic matrix components, e.g. silica, zinc oxide, zirconium oxide, clay (e.g. bentonite or attapulgite), silicates (e.g. calcium silicate) and mixtures thereof. In a preferred variant, silica may be provided to the wet material mixture from the source of silica sol.

Said manufacturing method or process further includes calcining the wet material mixture at a temperature, and for a time, sufficient to cure form a calcined hydrogenation pre-catalyst composition. In preferred variants for the purpose of the present invention, the calcining may occur at a temperature from about 300° C. to about 750° C. For example, in preferred variants for the purpose of the present invention, the calcining may occur at a temperature of about 300° C., about 350° C., about 400° C., about 450° C., about 500° C., about 550° C., about 600° C., about 650° C., about 700° C., about 750° C., or any range including and/or in between any two of the preceding values. In preferred variants for the purpose of the present invention, the calcining temperature may be in the range of from 400° C. to 650° C., preferably of from 400° C. to 550° C. and more preferably of from 450° C. to 500° C. In preferred variants for the purpose of the present invention, the calcination may occur over a period from about 0.5 h to about 4 h. In preferred variants for the purpose of the present invention, the calcination may occur over a period of about 0.5 h, about 1 h, about 1.5 h, about 2 h, about 2.5 h, about 3 h, about 3.5 h, about 4 h, or any range including and/or in between any two of the preceding values.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b) has a BET surface area of greater than about 30 $m^2/g$. In more preferred variants for the purpose of the present invention, the calcined hydrogenation pre-catalyst composition has a BET surface area of greater than about 45 $m^2/g$. In preferred variants for the purpose of the present invention, the calcined hydrogenation pre-catalyst composition has a BET surface area in the range of from 30 $m^2/g$ to 70 $m^2/g$. In more preferred variants for the purpose of the present invention, the calcined hydrogenation pre-catalyst composition has a BET surface area in the range of from 45 $m^2/g$ to 70 $m^2/g$. For example, in preferred variants for the purpose of the present invention, the calcined hydrogenation pre-catalyst composition has a BET surface area of about 30 $m^2/g$, about 35 $m^2/g$, about 40 $m^2/g$, about 45 $m^2/g$, about 50 $m^2/g$, about 55 $m^2/g$, about 60 $m^2/g$, about 65 $m^2/g$, about 70 $m^2/g$, or any range including and/or in between any two of the preceding values. In preferred variants for the purpose of the present invention, the calcined hydrogenation pre-catalyst composition has a BET surface area in the range of from 30 $m^2/g$ to 70 $m^2/g$, preferably of from 45 $m^2/g$ to about 65 $m^2/g$, more preferably of from 45 $m^2/g$ to 60 $m^2/g$ and even more preferably of from 50 $m^2/g$ to 60 $m^2/g$, or any range including and/or in between any two of the preceding values.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b) has a pore diameter in the range of from 150 to 2500 Angstroms (Å). For example, in preferred variants for the purpose of the present invention, the calcined hydrogenation pre-catalyst composition has a pore diameter in the range of from 150 Å to 2500 Å, preferably of from 200 Å to 2000 Å, more preferably of from 225 Å to 1500 Å, yet more preferably of from 250 Å to about 1000 Å and even yet more preferably of from 300 Å to 800 Å, or any range including and/or in between any two of the preceding values.

Pore diameters and pore volumes as defined in the present text are preferably measured utilizing mercury porosimetry. A typical method of conducting mercury porosimetry—which is also applicable for the purpose of the present invention—is described by R. Anderson, in "Experimental Methods in Catalytic Research", Academic Press, New York, 1968. The pore volumes are determined utilizing the pre-catalyst compositions (in their oxide forms). The pore diameters and pore volumes reported herein are obtained for a pre-catalyst composition after calcination, but prior to any reduction of the oxide (e.g. by hydrogenation). Those skilled in the art also sometimes refer to the pre-catalyst composition (containing metal oxides) as the "oxide" or "oxide precursor" form of a catalyst or catalyst composition.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b) has a pore volume that is greater than or equal to 0.25 $cm^3/g$. For example, in preferred variants for the purpose of the present invention, the calcined hydrogenation pre-catalyst composition may have a pore volume of about 0.25 $cm^3/g$, about 0.3 $cm^3/g$, about 0.35 $cm^3/g$, about 0.4 $cm^3/g$, about 0.45 $cm^3/g$, about 0.5 cm³/g, about 0.55 cm³/g, about 0.6 cm³/g, about 0.65 cm³/g, about 0.7 cm³/g, about 0.75 cm³/g, about 0.8 cm³/g, or any range including and/or in between any two of the preceding values. In preferred variants for the purpose of the present invention, the calcined hydrogenation pre-catalyst composition may have a pore volume in the range of from 0.25 cm³/g to 0.65 cm³/g, preferably of from 0.3 cm³/g to 0.55 cm³/g and more preferably of from 0.35 cm³/g to 0.45 cm³/g, or any range including and/or in between any two of the preceding values.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b) has a packed bulk density in the range of from 0.8 g/cm³ to 1.5 g/cm³.

For example, in preferred variants for the purpose of the present invention, the calcined hydrogenation pre-catalyst composition may have a packed bulk density of about 0.8 g/cm³, about 0.9 g/cm³, about 1 g/cm³, about 1.1 g/cm³, about 1.2 g/cm³, about 1.3 g/cm³, about 1.4 g/cm³, about 1.5 g/cm³, or any range including and/or in between any two of the preceding values. In preferred variants for the purpose of the present invention, the calcined hydrogenation pre-catalyst composition has a packed bulk density in the range of from 0.8 g/cm³ to 1.5 g/cm³, preferably of from 0.8 g/cm³ to 1 g/cm³ and more preferably of from 0.8 g/cm³ to 0.95 g/cm³, or any range including and/or in between any two of the preceding values.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b)—in an unactivated form—exhibits an X-ray powder diffraction profile comprising 2θ peaks at 26.7°, 29.6°, 35.5°, 38.7°, 58.9°, 53.4°, 68.2°, 61.6°, 66.3°, 68.0°, 72.3°, 75.1°, and 82.9°.

In preferred variants for the purpose of the present invention, the calcined hydrogenation pre-catalyst composition and/or the pre-catalyst composition which is suitable for use in the process according to the present invention or for use in a preferred process according to the present invention as defined above (in particular comprising pre-catalyst compositions PCC1a and PCC1b) has a copper oxide crystallite size in the range of from 60 Å to 200 Å. For example, in preferred variants for the purpose of the present invention, the calcined hydrogenation pre-catalyst composition may have a copper oxide crystallite size of about 60 Å, about 65 Å, about 70 Å, about 75 Å, about 80 Å, about 85 Å, about 90 Å, about 95 Å, about 100 Å, about 105 Å, about 110 Å, about 120 Å, about 125 Å, about 130 Å, about 135 Å, about 140 Å, about 145 Å, about 150 Å, about 155 Å, about 160 Å, about 165 Å, about 170 Å, about 175 Å, about 180 Å, about 185 Å, about 190 Å, about 195 Å, about 200 Å, or any range including and/or in between any two of the preceding values. In more preferred variants for the purpose of the present invention, the calcined hydrogenation pre-catalyst composition has a copper oxide crystallite size in the range of from 70 Å to 165 Å.

EXAMPLES

The following examples are meant to further explain and illustrate the present invention without limiting its scope.

Example 1: Pre-Catalyst Compositions

The pre-catalyst compositions PCC1a, PCC1b, PCC2, PCC3, PCC4, PCC5, PCC6 and PCC7 shown in tables 1a to 1c below were obtained from commercial sources (BASF SE, Germany). Pre-catalyst composition "PCC-EX" in table 1c is a hypothetical pre-catalyst composition only used for demonstrating purposes in the calculation example below.

TABLE 1a

Constituents of pre-catalyst compositions (mass-% of compositions)

| Composition: | PCC1a | PCC1b | PCC5 |
|---|---|---|---|
| Constituent | [mass-%] of the pre-catalyst composition | | |
| CuO | 75.0 | 75.0 | 60.0 |
| SiO$_2$ | 12.0-17.0 | 12.0-17.0 | 17.5-22.0 |
| MnO$_2$ | 1.0-5.0 | 1.0-5.0 | 0 |
| CaO and/or MgO and/or Na$_2$O | 5.0-10.0 | 5.0-10.0 | 20.0-24.0 |
| Formulation | Trilobed extrudates | Trilobed extrudates | Tablets |
| Formulation mean particle size | 1.5 mm | 3 mm | 5 mm |

TABLE 1b

Constituents of pre-catalyst compositions (mass-% of compositions)

| Composition: | PCC2 | PCC3 | PCC4 | PCC7 |
|---|---|---|---|---|
| Constituent | [mass-%] of the pre-catalyst composition | | | |
| CuO | 70.0 | 60.0 | 55.0 | 67.0 |
| Al$_2$O$_3$ | 3.0-10.0 | 27.0-32.0 | 42.0-45.0 | 26.0-30.0 |
| MnO$_2$ | 0 | 8.0-13.0 | 0 | 0 |
| ZnO | 20.0-25.0 | 0 | 0 | 0 |
| CaO and/or MgO and/or Na$_2$O | 0 | 0 | ≤1.0 | 0 |
| La$_2$O$_3$ | 0 | 0 | 0 | 3.0-7.0 |
| Formulation | Tablets | Tablets | Tablets | Tablets |
| Formulation mean particle size | 1.5 mm | 3 mm | 3 mm | 3 mm |

TABLE 1c

Constituents of pre-catalyst compositions (mass-% of compositions)

| Composition: | PCC6 | PCC-EX |
|---|---|---|
| Constituent | [mass-%] of the pre-catalyst composition | |
| CuO | 45.0 | 75.0 |
| SiO$_2$ | 0 | 15.0 |
| ZnO | 0 | 5.0 |
| Na$_2$O | 0 | 1.0 |
| BaO | 5.0-10.0 | 4.0 |
| Cr$_2$O$_3$ | 40.0-45.0 | 0 |
| Graphite | 1.0-5.0 | 0 |
| Formulation | Tablets | Tablets |
| Formulation mean particle size | 3 mm | 3 mm |

Composition PCC2 is e.g. commercially available from BASF SE under the trade name PURISTAR R3-30 T5X5; CuZn. Composition PCC3 is e.g. commercially available from BASF SE under the trade name Cu 0540 T (⅛)". Composition PCC4 is e.g. commercially available from BASF SE under the trade name H3-82 T3X3. Composition PCC5 is e.g. commercially available from BASF SE. Composition PCC6 is e.g. commercially available from BASF SE under the trade name E 406T (⅛)"; CuCr. Composition PCC7 is e.g. commercially available from BASF SE under the trade name H9-66 T3X3 (⅛)".

As reference, a commercially available nickel catalyst (Raney® nickel) was used.

For comparison, additional hydrogenation experiments were carried out using the following pre-catalyst compositions or catalyst compositions, respectively, not according to the invention:

1) Pd/C (commercially available) and
2) "NiO" (composition of "NiO" pre-catalyst composition: 16.7 mass-% CuO, 50.6 mass-% NiO, 1.5 mass-% $MoO_3$, 31.0 mass-% $ZrO_2$); the pre-catalyst composition "NiO" is per se known in the art. The catalytic hydrogenation reactions performed with this pre-catalyst composition were carried out according to procedures known in the art and similar to those described in this text (see examples 2 and 3).

Example 2: Activation of Pre-Catalyst Compositions to Catalyst Compositions (Steps S1) and S2))

A pre-catalyst composition as defined in tables 1a to 1c above was provided as fixed-bed catalyst under a nitrogen gas atmosphere (close to atmospheric pressure or at slight over pressure) and heated at a rate of 25° C./h to 50° C./h until the minimum activation temperature was reached. The minimum activation temperature ("$T_{act}$") applied in each case is shown in table 2 below.

The pre-catalyst composition was then activated by slow, stepwise addition of hydrogen gas until a concentration of 95 vol.-% of hydrogen (relative to the total volume of gases present) was achieved. The addition of hydrogen gas was controlled to limit the temperature increase over the reactor to 15° C. to 20° C. For the duration of the activation and reduction of the pre-catalyst composition the temperature was kept below the maximum temperature ("$T_{max}$") per pre-catalyst composition (applicable maximum temperatures per pre-catalyst composition are shown in table 2 below).

After the target concentration of hydrogen gas was reached and all exotherms had passed through the bed, the pre-catalyst composition was slowly heated to the respective hold temperature per pre-catalyst composition ("$T_{hold}$", see table 2 below for applicable hold temperatures per pre-catalyst compositions).

After this activation step, the resulting catalyst composition was cooled in a hydrogen atmosphere (as defined above) to a temperature of 100° C. or below, before it was used for the hydrogenation reaction (step S3)).

TABLE 2

Pre-catalyst composition activation processes and resulting catalyst compositions

| Pre-Catalyst Composition: | $T_{act}$ [° C.] | $T_{max}$ [° C.] | $T_{hold}$ [° C.] | Resulting Catalyst Composition: |
|---|---|---|---|---|
| PCC1a | 195 | 215 | 220 | CC1a |
| PCC1b | 195 | 215 | 220 | CC1b |
| PCC2 | 195 | 215 | 220 | CC2 |
| PCC3 | 175 | 215 | 200 | CC3 |
| PCC5 | 195 | 215 | 220 | CC5 |
| PCC6 | 140 | 175 | 180 | CC6 |

Calculation Examples

1) Total Amount of Copper in a Catalyst Composition:

Below is provided an example for calculating the total amount of copper in an exemplary (hypothetical) catalyst composition as may be used in the process of the present invention, relative to the total mass of metals present in the catalyst composition, as the ratio of the mass of copper atoms present in the catalyst composition, divided by the total mass of metal atoms present in the catalyst composition, based on a hypothetical catalyst composition "CC-EX" (resulting from activation of a hypothetical pre-catalyst composition PCC-EX, see table 1c above):

Since catalyst composition "CC-EX" is hypothetically made from pre-catalyst composition "PCC-EX" (which contains 75 mass-% of CuO), its (relative) molar amount of copper is 0.942 mole/100 g of catalyst composition (calculated as [mass of CuO in 100 g of pre-catalyst composition]/[molar mass of CuO]=75 g/79.55 g/mol), corresponding to 59.68 g of copper/100 g of pre-catalyst composition.

Since the (molar) amounts of metals (metal atoms) do not change when preparing a catalyst composition from a pre-catalyst composition according to the process of the present invention, the above masses of metal atoms given for a particular pre-catalyst composition (e.g. PCC-EX) do also apply for the respective catalyst composition made from said particular pre-catalyst composition (e.g. CC-EX).

Analogous calculation as shown above give the following masses of metals (or metal atoms) per 100 g of catalyst composition CC-EX:

| | |
|---|---|
| Copper: | 59.68 g |
| Zinc: | 4.01 g |
| Barium: | 3.58 g |
| Sodium: | 0.74 g |
| Sum: | 68.01 g |

The total amount of copper (or copper atoms) in catalyst composition CC-EX, relative to the total mass of metals (or metal atoms) present in the catalyst composition, is therefore 59.68 g/68.01 g=87.8 mass-%.

2) Total Amount of Substances Comprised by a Carrier Component (Component c2)) of a Catalyst Composition:

Below is provided an example for calculating the total amount of aluminium, silicon, zirconium and carbon in a catalyst composition, relative to the total mass of copper present in the catalyst composition, as the ratio of the total mass of aluminium atoms, silicon atoms, zirconium atoms and carbon atoms present in the catalyst composition, divided by the total mass of copper atoms present in the catalyst composition, based on catalyst composition CC-EX:

The total mass of aluminium atoms, silicon atoms, zirconium atoms and carbon atoms present in 100 g of catalyst composition (according to calculation as set out in calculation example 1, above) CC-EX is 7.02 g (i.e. 7.02 g of silicon atoms, as no atoms of aluminium, zirconium or carbon/graphite are present in CC-EX).

The total amount of of aluminium, silicon, zirconium and carbon (respectively of their atoms) in catalyst composition CC-EX, relative to the total mass of copper (or copper atoms) present in the catalyst composition, is therefore 7.02 g/59.68 g=11.8 mass-%.

3) Total Amount of One or More Metals not Selected from the Group Consisting of Copper, Aluminium and Zirconium (Component c3)) of a Catalyst Composition:

Below is provided an example for calculating the total amount of one or more metals not selected from the group consisting of copper, aluminium and zirconium in a catalyst composition, relative to the total mass of metals present in the catalyst composition, as the ratio of the mass of atoms of the one or more metals not selected from the group consisting of copper, aluminium and zirconium present in the catalyst composition divided by the total mass of metal atoms present in the catalyst composition, based on catalyst composition CC-EX:

The total mass of the one or more metals (or metal atoms) not selected from the group consisting of copper, aluminium and zirconium present in the catalyst composition is the sum of the masses of zinc (atoms) plus barium (atoms) plus sodium (atoms) (per 100 g of composition CC-EX):

4.01 g+3.57 g+0.74 g=8.32 g

The total amount of one or more metals (or metal atoms) not selected from the group consisting of copper, aluminium and zirconium, in catalyst composition CC-EX, relative to the total mass of metals present in composition CC-EX, is therefore 8.32 g/68.01 g=12.2 mass-%.

A similar activation procedure as set out above was carried out with the NiO pre-catalyst composition and resulted in activated NiO catalyst compositions, as is known in the art.

In the reference pre-catalyst composition comprising Raney® nickel, the pre-catalyst composition was prepared in a usual manner known in the art, e.g. as disclosed in document EP 0 358 420 A2.

Pd/C was prepared for the reaction in a usual manner as is known in the art.

Example 3: Catalytic Hydrogenation of 1-(4-isobutylphenyl)ethanone with Catalyst Compositions in a Batch Process A catalyst composition (for preparation see example 2 above, for applicable catalyst compositions used in this experiment see table 3 below) was added to an autoclave containing 1-(4-isobutylphenyl)ethanone, in an amount of 2 mass-% relative to the total mass of 1-(4-isobutylphenyl)ethanone present in the autoclave (mass calculation for the catalyst composition was based on the pre-catalyst composition used). The autoclave was pressurized with nitrogen gas to a pressure of 10 MPa and depressurized (to atmospheric pressure) again. This process was repeated 3 times. Then, the depressurized autoclave (flooded with nitrogen gas after the last depressurization) was pressurized with hydrogen gas to a pressure of 4.0 MPa and the reaction vessel of the autoclave was heated to a temperature of 100° C. under stirring for the hydrogenation process. The stirring was continued for 8 h before the autoclave was cooled to room temperature (20° C.) and depressurized to atmospheric pressure.

Catalyst compositions CC1a, CC2 and CC7 were prepared by the activation procedure as described in example 2 from pre-catalyst compositions PCCa1, PCC2 and PCC7, respectively.

After the hydrogenation process was completed, a sample of the final product was drawn from the reaction mixture and analyzed by gas chromatography. The area-% found for the product 1-(4-isobutylphenyl)ethanol was recorded and used for calculation of yield, selectivity for the main product 1-(4-isobutylphenyl)ethanol (shown in tables 3-8 as "selectivity for IBPE"), selectivity for the side product 1-ethyl-4-isobutylbenzene (shown in tables 3-8 as "selectivity for EIBB") and conversion (as defined above). The resulting values are shown in table 3 below.

The reference hydrogenation process using Raney® nickel as catalyst composition was conducted in a manner as is known in the art, e.g. as disclosed in document EP 0 358 420 A2. The resulting values are also shown in table 3 below.

Further hydrogenation experiments were conducted with catalyst compositions as shown in table 3 below (NiO, Pd/C, see above). Hydrogenation with the NiO-catalyst was carried out under conditions equal to the conditions indicated in example 3 (above). Hydrogenation with the Pd/C catalyst was carried out in a usual manner as is known in the art. The respective results are also reported in table 3 below.

TABLE 3

Results of catalytic hydrogenation of 1-(4-isobutylphenyl)ethanone in a batch process

| Catalyst Composition: | Selectivity for IBPE [%] | Selectivity for EIBB [%] | Conversion [%] | Yield [%] |
|---|---|---|---|---|
| CC1a | >99.9 | 0 | 70 | 70 |
| CC2 | 98 | 1.8 | 99 | 97 |
| CC7 | >99.9 | 0 | 55 | 55 |
| Raney ®-nickel (comparison) | 90 | 9.5 | 98 | 88 |
| "NiO" (comparison) | 20 | 80 | 15 | 3 |
| Pd/C (comparison) | Rapid isomerization of starting compound (e.g. into 3-isobutylacetophenone, 4-n-butylacetophenone, etc.) | | | |

From the results shown in table 3 above it can be seen that processes using comparative catalyst compositions "Pd/C" and "NiO" (both not according to the invention) were not suited for catalyzing the selective hydrogenation of 1-(4-isobutylphenyl)ethanone.

Processes using catalyst compositions (or pre-catalyst compositions, respectively) CC1a, CC2 and CC7 on the other hand were well suited to selectively hydrogenate 1-(4-isobutylphenyl)ethanone in a batch process with selectivities equal or higher than the reference process using Raney® nickel as catalyst composition, however, with varying degrees of conversion and yield.

As Raney® nickel is provided in powder form, it is not suited to be used in a fixed-bed reactor and thus not suited for use in a continuous catalytic hydrogenation process.

Example 4: Catalytic Hydrogenation of 1-(4-isobutylphenyl)ethanone with Catalyst Compositions in a Continuous Process A continuous reactor (inner diameter: 8 mm, length: 1 m) equipped with a recycle-loop, a separator after the reactor and a heater for heating the starting compound (1-(4-isobutylphenyl)ethanone) was loaded with 30.0 g of a pre-catalyst composition (for applicable pre-catalyst compositions used in this experiment see tables 1a to 1c above and table 4 below).

The reactor system (reactor, recycle-loop, separator and heater) was flushed with nitrogen gas at room temperature (20° C.) and atmospheric pressure. Then, the pre-catalyst composition in the reactor was activated as described in example 2 above to result in the respective catalyst compositions as set out in table 2 above. When the activation process was completed, the reactor was pressurized with hydrogen gas to a pressure of 4.0 MPa and the temperature was raised to 120° C. When the target pressure and temperature were reached, the starting compound (1-(4-isobutylphenyl)ethanone) was fed into the reactor continuously at a rate of 5 g/h to 100 g/h.

During the hydrogenation experiment, samples were drawn from the reactor in regular intervals and analyzed by gas chromatography. The area-% found for the product 1-(4-isobutylphenyl)ethanol and for the side product 1-ethyl-4-isobutylbenzene in each case was recorded and used for calculation of yield, selectivity and conversion (see example 3, above). The resulting values are shown in table 4 below.

The recycle ratio was 4:1.

TABLE 4

Results of catalytic hydrogenation of 1-(4-isobutylphenyl)ethanone to 1-(4-iso-butylphenyl) ethanol in a continuous process

| Pre-Catalyst Composition: | Catalyst Composition: | Selectivity for IBPE [%] | Selectivity for EIBB [%] | Conversion [%] | Yield [%] |
|---|---|---|---|---|---|
| PCC1a | CC1a | >99.9 | <0.1 | 98 | 98 |
| PCC1b | CC1b | 99.7 | 0.2 | 95 | 95 |
| PCC2 | CC2 | 94 | 5.5 | 98 | 92 |
| PCC3 | CC3 | 99.7 | 0.2 | 92 | 92 |
| PCC4 | CC4 | 95 | 4.5 | 95 | 90 |
| PCC5 | CC5 | 98 | 1.5 | 82 | 80 |
| PCC6 | CC6 | 97 | 2.5 | 88 | 85 |

From the results shown in table 4 above it can be seen that all catalyst compositions (or pre-catalyst compositions, respectively) used were suited for catalyzing the hydrogenation of 1-(4-isobutylphenyl)ethanone in a continuous process with high selectivity (≥94%) and acceptable to high conversion to and yield of 1-(4-isobutylphenyl)ethanol. Highest selectivity at high conversion and yield was obtained when using catalyst compositions CC1a, CC1b and CC3, all comprising manganese oxide (as metal other than copper) and silicon or a silicon compound (from $SiO_2$) or aluminium or an aluminium compound (from $Al_2O_3$) as substances of the carrier component. Best results in terms of selectivity, conversion and yield were obtained with catalyst compositions CC1a and CC1b with the results obtained with catalyst composition CC1a yet exceeding the results obtained with catalyst composition CC1b.

Example 5: Catalytic Hydrogenation of 1-(4-isobutylphenyl)ethanone in a Long-Term Continuous Process at Varying Temperature A continuous reactor as described in example 4 above, but with the following modifications:
inner diameter of reactor: 2.16 mm; length: 31 m
after the separator, a second reactor ("post-reactor") was positioned with the same dimensions as the first reactor;
was used for a long-term hydrogenation experiment. The continuous hydrogenation reaction was carried out as described in example 4 above with the pre-catalyst composition PCC1a (corresponding to catalyst composition CC1a, see example 4 and table 4 above), for a period of >8000 h.

The pre-catalyst composition was used in an amount ("pre-catalyst load") of 1.0 kg [1-(4-isobutylphenyl)ethanone]/(kg pre-catalyst*h) and this amount (or ratio) was held constant for the duration of the long-term hydrogenation experiment.

The hydrogen gas pressure applied was 3.5 MPa and was also held constant for the duration of the long-term hydrogenation experiment.

The temperature was varied during the hydrogenation process (step S3)) in a range from 30° C. to 200° C.

During the hydrogenation experiment, samples were drawn from the reactor in regular intervals and analyzed by gas chromatography as explained in example 4 above. The area-% found for the product 1-(4-isobutylphenyl)ethanol and for the side product 1-ethyl-4-isobutylbenzene in each case was recorded and used for calculation of selectivity and conversion (see example 3, above). The resulting values are shown in table 5 below.

The recycle ratio was 1:1.

TABLE 5

Results of catalytic hydrogenation of 1-(4-isobutylphenyl) ethanone in a long-term continuous process with pre-catalyst composition PCC1a at constant pre-catalyst load (varying temperature)

| Temperature [° C.] | Selectivity for IBPE [%] | Selectivity for EIBB [%] | Conversion [%] |
|---|---|---|---|
| 30 | 100 | 0 | 12 |
| 60 | 100 | 0 | 95 |
| 100 | 100 | 0 | 99 |
| 120 | 99 | 0.7 | 99 |
| 150 | 96 | 3.8 | 98 |
| 200 | 81 | 18 | 94 |

From the results shown in table 5 it can be seen that best results of the process according to the invention in terms of combined optimized values for conversion and selectivity (for the main product 1-(4-isobutylphenyl)ethanol) of the process are obtained in the temperature range of from 50° C. to 200° C., preferably of from 90° C. to 150° C., more preferably of from 100° C. to 130° C. in step S3).

Below a temperature of 50° C., preferably of 90° C., more preferably of 100° C., conversion of the starting compound had not reached its maximum yet. Above a temperature of 200° C., preferably of 150° C., more preferably of 130° C., conversion of the starting compound was declining again from the range of optimal conversion.

Example 6: Catalytic Hydrogenation of 1-(4-isobutylphenyl)ethanone in a Long-Term Continuous Process at Varying Pressure A continuous reactor as described in example 5 above was used for a long-term hydrogenation experiment. The continuous hydrogenation reaction was carried out as described in example 4 above with the pre-catalyst composition PCC1a (corresponding to catalyst composition CC1a, see example 4 and table 4 above), for a period of >8000 h.

The pre-catalyst composition was used in an amount ("pre-catalyst load") of 2.0 kg [1-(4-isobutylphenyl)ethanone]/(kg pre-catalyst composition*h) and this amount (or ratio) was held constant for the duration of the long-term hydrogenation experiment.

The temperature applied was set to 120° C. and was held constant for the duration of the long-term hydrogenation experiment.

The pressure was varied during the hydrogenation process (step S3)) in a range from 0.5 MPa to 10 MPa.

During the hydrogenation experiment, samples were drawn from the reactor in regular intervals and analyzed by gas chromatography as explained in example 4 above. The area-% found for the product 1-(4-isobutylphenyl)ethanol and for the side product 1-ethyl-4-isobutylbenzene in each case was recorded and used for calculation of selectivity and conversion (see example 3, above). The resulting values are shown in table 6 below.

The recycle ratio was 4:1.

TABLE 6

Results of catalytic hydrogenation of 1-(4-isobutylphenyl) ethanone in a long-term continuous process with pre-catalyst composition PCC1a at constant pre-catalyst load (varying hydrogen pressure)

| Hydrogen pressure [MPa] | Selectivity for IBPE [%] | Selectivity for EIBB [%] | Conversion [%] |
| --- | --- | --- | --- |
| 0.5 | 100 | 0 | 58 |
| 1.5 | 100 | 0 | 80 |
| 2.5 | 100 | 0 | 82 |
| 3.5 | 99 | 0.7 | 99 |
| 4.0 | 99 | 0.7 | 99 |
| 10.0 | 95 | 5 | 100 |

The results shown in table 6 illustrate that best results of the process according to the invention in terms of combined optimized values for conversion and selectivity (for the main product 1-(4-isobutylphenyl)ethanol) of the process are obtained in the pressure range of from 0.5 to 8.0 MPa, preferably of from 1.5 to 4.5 MPa and more preferably of from 2.5 to 4.25 MPa.

Example 7: Catalytic Hydrogenation of 1-(4-isobutylphenyl)ethanone in a Long-Term Continuous Process at Varying Pre-Catalyst Composition Load A long-term hydrogenation experiment was carried out as described in example 5 above, with the following modifications in the reaction set-up:

The temperature applied during the hydrogenation process (step S3) was set to 120° C. and was held constant for the duration of the long-term hydrogenation experiment.

The amount (or ratio) of pre-catalyst composition PCC1a used in the long-term hydrogenation experiment ("pre-catalyst load") was varied during the hydrogenation process (step S3)) in a range of from 1.0 kg [1-(4-isobutylphenyl)ethanone]/(kg pre-catalyst composition*h) to 3.0 kg [1-(4-isobutylphenyl)ethanone]/(kg pre-catalyst composition*h).

During the hydrogenation experiment, samples were drawn from the reactor in regular intervals and analyzed by gas chromatography as explained in example 4 above. The area-% found for the product 1-(4-isobutylphenyl)ethanol and for the side product 1-ethyl-4-isobutylbenzene in each case was recorded and used for calculation of selectivity and conversion (see example 3, above). The resulting values are shown in table 7 below.

The recycle ratio was 1:1.

TABLE 7

Results of catalytic hydrogenation of 1-(4-isobutylphenyl) ethanone in a long-term continuous process with pre-catalyst composition PCC1a at constant temperature (varying pre-catalyst composition load)

| Pre-catalyst load [kg[1-(4-isobutyl-phenyl)ethanone]/ (kg pre-catalyst composition*h) | Selectivity for IBPE [%] | Selectivity for EIBB [%] | Conversion [%] |
| --- | --- | --- | --- |
| 1.0 | 99 | 0.7 | 99 |
| 1.5 | 100 | 0 | 97 |
| 2.0 | 100 | 0 | 95 |
| 2.5 | 100 | 0 | 86 |
| 3.0 | 100 | 0 | 82 |

From the results shown in table 7 it can be seen that conducting a continuous process according to the invention with a total amount of pre-catalyst composition in the range of from 0.1 kg [1-(4-isobutylphenyl)ethanone]/(kg pre-catalyst composition*h) to 5.0 kg [1-(4-isobutylphenyl)ethanone]/(kg pre-catalyst composition*h), preferably of from 0.5 kg [1-(4-isobutylphenyl)ethanone]/(kg pre-catalyst composition*h) to 3.0 kg [1-(4-isobutylphenyl)ethanone]/(kg pre-catalyst composition*h), more preferably of from 1.0 kg [1-(4-isobutylphenyl)ethanone]/(kg pre-catalyst composition*h) to 2.5 kg [1-(4-isobutylphenyl)ethanone]/(kg pre-catalyst composition*h), where the kg [1-(4-isobutylphenyl)ethanone] is the amount of 1-(4-isobutylphenyl)ethanone present at the start of the reaction (step S2)) ("pre-catalyst load") brought about the best results in terms of conversion to the main product.

In the further optimized range of pre-catalyst loads (as shown in table 7 above as a detailed view on the most preferred range of pre-catalyst amounts to be used), at pre-catalyst load rates below 1.0 kg [1-(4-isobutylphenyl)ethanone]/(kg pre-catalyst composition*h), preferably below 1.25 kg [1-(4-isobutylphenyl)ethanone]/(kg pre-catalyst composition*h), product selectivity had not reached its maximum value. At pre-catalyst load rates above 2.5 kg [1-(4-isobutylphenyl)ethanone]/(kg pre-catalyst composition*h), preferably above 2.25 kg [1-(4-isobutylphenyl)ethanone]/(kg pre-catalyst*h), conversion to the main product decreased from its maximum value.

Example 8: Catalytic Hydrogenation of 1-(4-isobutylphenyl)ethanone in a Long-Term Continuous Process at Varying Reaction Time A long-term hydrogenation experiment was carried out as described in example 5 above, with the following modifications in the reaction set-up:

The temperature applied during the hydrogenation process (step S3) was set to 100° C. and was held constant for the duration of the long-term hydrogenation experiment.

The amount (or ratio) of pre-catalyst composition PCC1a used in the long-term hydrogenation experiment ("pre-catalyst load") was held constant during the hydrogenation process (step S3)) at 1.0 kg [1-(4-isobutylphenyl)ethanone]/(kg pre-catalyst*h).

During the hydrogenation experiment, samples were drawn from the reactor in regular intervals and analyzed by gas chromatography as explained in example 4 above. The area-% found for the product 1-(4-isobutylphenyl)ethanol in each case was recorded and used for calculation of selectivity and conversion. The resulting values are shown in table 8 below.

TABLE 8

Results of catalytic hydrogenation of 1-(4-isobutylphenyl) ethanone in a long-term continuous process with pre-catalyst composition PCC1a at constant temperature (varying reaction time)

| Reaction time ("time on stream") [h] | Selectivity for IBPE [%] | Selectivity for EIBB [%] | Conversion [%] |
|---|---|---|---|
| 50 | 99 | 0.7 | 99 |
| 1000 | 100 | 0 | 99 |
| 3000 | 100 | 0 | 99 |
| 5000 | 100 | 0 | 99 |
| 9500 | 100 | 0 | 99 |

From the results shown in table 8 it can be seen that a continuous process according to the invention with an optimized total amount of pre-catalyst composition and an optimized reaction temperature is suited for being conducted over extended time periods (>8000 h) without reduction in quality of the process parameters, in particular of selectivity and conversion of the hydrogenation process according to the invention. The process according to the present invention is therefore particularly suited for being conducted as a long-time, continuous industrial process.

Example 9: Preparation of Pre-Catalyst Compositions Suitable for Use in the Process of the Present Invention Pre-catalyst compositions which are suitable for use in the process according to the present invention or in a preferred process according to the present invention as defined above (comprising pre-catalyst compositions of the type and of at least similar quality of performance in the process of the present invention as pre-catalyst compositions PCC1a and PCC1b with respect to beneficial selectivity, conversion and/or yield in the hydrogenation of 1-(4-isobutylphenyl) ethanone to 1-(4-isobutylphenyl)ethanol) having varying levels of copper oxide, sodium oxide and surface area were prepared as follows: copper oxide, clay, calcium hydroxide (lime), alkali metal source (sodium hydroxide), manganese oxide, and silica sol were mixed and kneaded. The mixture was then extruded with an extruder and dried at a temperature in the range of from 55° C. to 120° C. The extrudates were then calcined at a temperature in the range of from 450-600° C. to a desired surface area. The pre-catalyst compositions PCC8-1A to PCC8-1K had the properties outlined in Tables 9a to 9c, where "3F" means "3-fluted" or "tri-lobe".

In tables 9a to 9c, the analysis for the mass percentages of the constituents $CuO$, $SiO_2$, $CaO$, $MnO_2$ and $Na_2O$ was conducted at a temperature of 650° C. in each case, as indicated in the tables.

TABLE 9a

Properties of different pre-catalyst compositions after their preparation (1)

| Pre-Catalyst Composition: | PCC8-1A | PCC8-1B | PCC8-1C | PCC8-1D |
|---|---|---|---|---|
| Mass-% CuO at 650° C. | 74.1 | 74.1 | 74.1 | 74.1 |
| Mass-% $SiO_2$ at 650° C. | 13.2 | 13.2 | 13.2 | 13.2 |
| Mass-% CaO at 650° C. | 5.7 | 5.7 | 5.7 | 5.7 |
| Mass-% $MnO_2$ at 650° C. | 0.9 | 0.9 | 0.9 | 0.9 |
| Mass-% $Na_2O$ at 650° C. | 3.3 | 3.3 | 3.3 | 3.3 |
| Size/shape (3F) | 1/16" | 1/16" | 1/16" | 1/16" |
| BET surface area [m²/g] | 46 | 52 | 35 | 20 |
| Hg pore volume [cm³/g] | 0.40 | 0.39 | 0.38 | 0.32 |
| Average pore diameter [Å] | 344 | 303 | 442 | 631 |
| Packed bulk density [g/cm³] | 0.95 | 0.94 | 0.97 | 1.08 |
| Calcination temperature [° C.] | 500 | 450 | 550 | 600 |

TABLE 9b

Properties of different pre-catalyst compositions after their preparation (2)

| Pre-Catalyst Composition: | PCC8-1E | PCC8-1F | PCC8-1G | PCC8-1H |
|---|---|---|---|---|
| Mass-% CuO at 650° C. | 73.3 | 72.9 | 72.3 | 70.5 |
| Mass-% $SiO_2$ at 650° C. | 13.2 | 13.2 | 13.2 | 12.4 |
| Mass-% Ca at 650° C. | 6.2 | 6.2 | 6.2 | 6.0 |
| Mass-% $MnO_2$ at 650° C. | 0.9 | 1.0 | 1.9 | 4.3 |
| Mass-% $Na_2O$ at 650° C. | 3.3 | 3.3 | 3.2 | 3.3 |
| Size/shape (3F) | 1/16" | 1/16" | 1/16" | 1/16" |
| BET surface area [m²/g] | 36 | 34 | 32 | 36 |
| Hg pore volume [cm³/g] | 0.41 | 0.41 | 0.43 | 0.37 |
| Average pore diameter [Å] | 453 | 485 | 782 | 542 |
| Packed bulk density [g/cm³] | 0.93 | 0.91 | 0.87 | 0.95 |
| Calcination temperature [° C.] | 550 | 550 | 550 | 550 |

TABLE 9c

Properties of different pre-catalyst compositions after their preparation (3)

| Pre-Catalyst Composition: | PCC8-1I | PCC8-1J | PCC8-1K |
|---|---|---|---|
| Mass-% CuO at 650° C. | 74.1 | 74.2 | 73.8 |
| Mass-% $SiO_2$ at 650° C. | 13.5 | 13.2 | 13.9 |
| Mass-% CaO at 650° C. | 6.3 | 5.9 | 6.4 |

TABLE 9c-continued

Properties of different pre-catalyst compositions after their preparation (3)

| Pre-Catalyst Composition: | PCC8-1I | PCC8-1J | PCC8-1K |
|---|---|---|---|
| Mass-% $MnO_2$ at 650° C. | 0 | 1.9 | 1.1 |
| Mass-% $Na_2O$ at 650° C. | 3.4 | 3.7 | 3.8 |
| Size/shape (3F) | 1/16" | 1/16" | 1/16" |
| BET surface area [m²/g] | 29 | 43 | 30 |
| Hg pore volume [cm³/g] | 0.36 | 0.38 | 0.38 |
| Average pore diameter [Å] | 713 | 401 | 440 |
| Packed bulk density [g/cm³] | 0.95 | 0.93 | 0.99 |
| Calcination temperature [° C.] | 550 | 500 | 500-550 |

Example 10: X-Ray Diffraction Analysis of Pre-Catalyst Compositions

A PANalytical MPD X'Pert Pro diffraction system was used to collect data for exemplary pre-catalyst compositions PCC8-1A to PCC8-1D. Cu $K_\alpha$-radiation was used in the analysis with generator settings of 45 kV and 40 mA. The optical path consisted of a 1° divergence slit, 2° anti-scatter slit, the sample, and an X'Celerator position sensitive detector. Each pre-catalyst composition sample was first prepared by backpacking the sample into round mount. The data collection from the round mount covered a range from 10° to 90° 2θ using a step scan with a step size of 0.017° 2θ and a scan speed of 0.036° 2θ per second. The X'Pert Pro HighScore program was used for phase identification analysis.

It was found in this experiment that monoclinic copper oxide (CuO; 00-048-1548) was the predominant phase for exemplary pre-catalyst compositions PCC8-1A to PCC8-1D. The copper oxide crystallite sizes for exemplary pre-catalyst compositions PCC8-1A to PCC8-1D are shown in table 10 below:

TABLE 10

Copper oxide crystallite sizes of pre-catalyst compositions

| Pre-Catalyst Composition: | PCC8-1A | PCC8-1B | PCC8-1C | PCC8-1D |
|---|---|---|---|---|
| Copper oxide crystallite size [Å] | 81 ± 5 | 78 ± 5 | 83 ± 5 | 160 ± 5 |

It was further found that orthorhombic sodium silicate ($Na_2SiO_3$; 04-008-2078) is present as a minor phase with its strongest reflection (020) matching up at 29° 2θ. Hexagonal silica ($SiO_2$; 01-075-3165) was observed around 27° 2θ. The full listing of 2θ peaks is: 26.7°, 29.6°, 35.5°, 38.7°, 58.9°, 53.4°, 68.2°, 61.6°, 66.3°, 68.0°, 72.3°, 75.1°, and 82.9°.

The invention claimed is:

1. A process for producing 1-(4-isobutylphenyl) ethanol comprising:
   S3) reacting 1-(4-isobutylphenyl)ethenone with hydrogen in the presence of a catalyst composition comprising copper and one or more metal other than copper, wherein the catalyst composition comprises
   c1) the copper in a total amount in a range of from 65 mass-% to 92.5 mass-%, relative to the total mass of metals present in the catalyst composition;
   c2) a carrier component comprising one or more substance selected from the group consisting of silicon and silicon compounds, wherein a total amount of silicon in the catalyst composition, relative to the total mass of copper present in the catalyst composition, is in a range of from 3.5 mass-% to 15.0 mass-%;
   and
   c3) manganese in a total amount in a range of from 0.75 mass-% to 3.15 mass-%, relative to the total mass of metals present in the catalyst composition;
   and
   one or more metal selected from the group consisting of sodium and calcium, wherein a total amount of the one or more metal selected from the group consisting of sodium and calcium in the catalyst composition, relative to the total mass of metals present in the catalyst composition, is in a range of from 4.5 mass-% to 15.0 mass-%; and
   wherein the catalyst composition has a molar ratio of copper:aluminum of ≥10.

2. The process according to claim 1, wherein the catalyst composition comprises:
   c1') copper in the total amount in a range of from 65 mass-% to 92.5 mass-%, relative to the total mass of metals present in the catalyst composition;
   c2') a carrier component comprising one or more substance selected from the group consisting of silicon and silicon compounds, wherein a total amount of silicon in the catalyst composition, relative to the total mass of copper present in the catalyst composition, is in a range of from 5.0 mass-% to 15.0 mass-%;
   and
   c3') manganese in the total amount in a range of from 0.75 mass-% to 3.15 mass-%, relative to the total mass of metals present in the catalyst composition; and
   one or more metal selected from the group consisting of sodium and calcium, wherein a total amount of the one or more metals selected from the group consisting of sodium and calcium in the catalyst composition, relative to the total mass of metals present in the catalyst composition, is in a range of from 7.5 mass-% to 12.5 mass-%.

3. The process according to claim 1, wherein added masses of components c1) and c3) present in the catalyst composition make up a total mass of metals present in the catalyst composition.

4. The process according to claim 1, wherein in the catalyst composition a molar ratio of:
   copper:nickel is >10;
   and/or
   copper:chromium is >10;
   and/or
   copper: ruthenium is >10;
   and/or
   copper: palladium is >10
   and/or
   copper: graphite carbon is >50.

5. The process according to claim 1,
wherein
in the catalyst composition, a molar ratio of
copper:zinc is >10,
and/or
the 1-(4-isobutylphenyl) ethanone present in S3) comprises other organic and/or inorganic chemical compounds selected from the group consisting of acetic acid, acetates, fluorides, chlorides; oxygen-containing compounds selected from ketones, aldehydes, esters, ethers and water; nitrogen-containing compounds selected from amines, amides, urea compounds, nitrates, nitrites, and nitrosyl compounds; and sulfur-containing compounds selected from thiols, thio ethers, sulfides, sulfates, and sulfones,
in an amount of ≤10 mass-%, relative to the total mass of the 1-(4-isobutylphenyl) ethanone and the other organic and/or inorganic chemical compounds.

6. The process according to claim 1 wherein
the 1-(4-isobutylphenyl) ethanone is present in a liquid phase for at least a part of the process or process time of S3),
and/or
1-(4-isobutylphenyl) ethanone and/or 1-(4-isobutylphenyl) ethanol make up ≥90.0 vol.-% of a liquid phase in S3).

7. The process according to claim 1, wherein the reacting in S3) is carried out at least for a part of the process or process time:
at a hydrogen pressure in a range of from 0.5 to 8.0 MPa;
and/or
at a molar ratio of hydrogen to the 1-(4-isobutylphenyl) ethanone which is present at the start of S3) in a range of from 1 to 20;
and/or
at a temperature in the range of from 30° C. to 200° C.

8. The process according to claim 1, wherein
the reacting in S3) is carried out continuously for at least a part of the process or process time.

9. The process according to claim 8, wherein the reacting in S3) is carried out continuously for at least a part of the process or process time
in one or more fixed-bed reactors
and/or
in two or more serially connected reactors comprising one or more main reactors, each comprising one or more recycle loops or one combined recycle loop, and one or more post-reactors, not comprising recycle loops,
and/or
the catalyst composition is or comprises a fixed-bed catalyst or fixed-bed catalyst composition,
and/or
the catalyst load is in the range of from 0.1 kg [1-(4-isobutylphenyl) ethanone]/(kg catalyst composition*h) to 5.0 kg [1-(4-isobutylphenyl) ethanone]/(kg catalyst composition*h),
where the kg [1-(4-isobutylphenyl) ethanone] is the total amount of 1-(4-isobutylphenyl) ethanone present at the start of the reaction;
and/or
1-(4-isobutylphenyl) ethanone is continuously fed into or provided to reaction step S3) in an amount of ≤500 t/h.

10. The process according to claim 9, wherein the reacting in step S3) is carried out continuously for at least a part of the process or process time in two or more serially connected reactors comprising one or more main reactors, each comprising one or more recycle loops or one combined recycle loop, and one or more post-reactors, not comprising recycle loops, wherein a recycle ratio in the one or more recycle loops is in a range of from 0.1 to 20.

11. The process according to claim 1, further comprising before S3):
S1) providing or preparing a pre-catalyst composition comprising a mixture of oxides of copper and oxides of one or more metals other than copper,
wherein the pre-catalyst composition comprises oxides of copper in a total amount in a range of from 55 mass-% to 80 mass-%, relative to a total mass of the pre-catalyst composition;
and wherein the pre-catalyst composition comprises in addition to the oxides of copper:
p2) a carrier comprising oxides of silicon,
wherein a total amount of oxides of silicon in the pre-catalyst composition, relative to the total mass of the pre-catalyst composition, is in a range of from 3.0 mass-% to 35.0 mass-%;
and
p3) oxides of manganese, wherein a total amount of the oxides of manganese in the pre-catalyst composition, relative to the total mass of the pre-catalyst composition, is in a range of 0.5 mass-% to 5.0 mass-%,
and
oxides of one or more metal selected from the group consisting of sodium and calcium, wherein a total amount of the oxides of one or more metal selected from the group consisting of sodium and calcium, relative to the total mass of the pre-catalyst composition, is in a range of from 5.0 mass-% to 25.0 mass-%,
and
S2) reacting the pre-catalyst composition from step S1) with hydrogen at a temperature in a range of from 120° C. to 230° C.,
such that the catalyst composition comprising copper and one or more metal other than copper used in S3) results.

12. The process according to claim 11, wherein
the pre-catalyst composition is present for at least a part of the process or process time as a formulation of solid particles selected from the group consisting of extrudates, tablets, pellets, strands, stars, powders, granules, granulates, and mixtures thereof;
and/or
the reacting in step S2) is carried out for at least a part of the reaction or reaction time in the presence of a gaseous atmosphere comprising hydrogen gas and one or more other gases which are inert under the reaction conditions.

13. The process according to claim 12, wherein the pre-catalyst composition is present for at least a part of the process or process time as a formulation of solid particles selected from the group consisting of extrudates comprising trilobed extrudates; and tablets.

14. A catalytic hydrogenation process for producing 1-(4-isobutylphenyl) ethanol from 1-(4-isobutylphenyl) ethanone comprising the use of
a composition as defined in claim 1,
and/or
a pre-composition comprising
a mixture of oxides of copper and oxides of one or more metal other than copper, wherein the pre-composition comprises the oxides of copper in a total amount in a range of from 55 mass-% to 80 mass-%, relative to a total mass of the pre-composition, a carrier comprising oxides of silicon, wherein a total amount of oxides of silicon in the pre-catalyst composition, relative to the total mass of the pre-catalyst composition, is in a range of from 3.0 mass-% to 35.0 mass-%;

oxides of manganese, wherein a total amount of the oxides of manganese in the pre-catalyst composition, relative to the total mass of the pre-catalyst composition, is in a range of 0.5 mass-% to 5.0 mass-%; and oxides of one or more metal selected from the group consisting of sodium and calcium, wherein a total amount of the oxides of one or more metals selected from the group consisting of sodium and calcium, relative to the total mass of the pre-catalyst composition, is in a range of from 5.0 mass-% to 25.0 mass-%.

15. The process according to claim 14, wherein the catalytic hydrogenation process is at least partly performed as a continuous hydrogenation process, and/or the composition comprises a fixed-bed catalyst or fixed-bed catalyst composition and/or the pre-composition is provided in a fixed-bed.

\* \* \* \* \*

UNITED STATES PATENT AND TRADEMARK OFFICE
CERTIFICATE OF CORRECTION

PATENT NO. : 12,378,174 B2
APPLICATION NO. : 17/298692
DATED : August 5, 2025
INVENTOR(S) : Albert Werner et al.

Page 1 of 1

It is certified that error appears in the above-identified patent and that said Letters Patent is hereby corrected as shown below:

In the Claims

Claim 1, Column 40, Line 4:
Change "S3) reacting 1-(4-isobutylphenyl)ethenone with hydrogen" to --S3) reacting 1-(4-isobutylphenyl) ethanone with hydrogen--.

Signed and Sealed this
Twenty-eighth Day of October, 2025

John A. Squires
*Director of the United States Patent and Trademark Office*